(12) United States Patent
Van Tol et al.

(10) Patent No.: US 9,987,035 B2
(45) Date of Patent: Jun. 5, 2018

(54) SURGICAL INSTRUMENT WITH END-EFFECTOR ASSEMBLY INCLUDING THREE JAW MEMBERS AND METHODS OF CUTTING TISSUE USING SAME

(71) Applicant: COVIDIEN LP, Mansfield, MA (US)

(72) Inventors: David J. Van Tol, Boulder, CO (US); Anthony B. Ross, Boulder, CO (US); Alexander M. Waskiewicz, Lafayette, CO (US); Eric R. Larson, Boulder, CO (US)

(73) Assignee: COVIDIEN LP, Mansfield, MA (US)

( * ) Notice: Subject to any disclaimer, the term of this patent is extended or adjusted under 35 U.S.C. 154(b) by 539 days.

(21) Appl. No.: 14/548,560

(22) Filed: Nov. 20, 2014

(65) Prior Publication Data

US 2015/0150584 A1 Jun. 4, 2015

Related U.S. Application Data

(60) Provisional application No. 61/910,634, filed on Dec. 2, 2013.

(51) Int. Cl.
| | |
|---|---|
| *A61B 18/14* | (2006.01) |
| *A61B 17/32* | (2006.01) |
| *A61B 17/295* | (2006.01) |
| *A61B 18/00* | (2006.01) |
| *A61B 34/30* | (2016.01) |

(52) U.S. Cl.
CPC .... *A61B 17/320092* (2013.01); *A61B 17/295* (2013.01); *A61B 18/1445* (2013.01); *A61B 34/30* (2016.02); *A61B 2018/0063* (2013.01); *A61B 2018/00607* (2013.01); *A61B 2018/1455* (2013.01)

(58) Field of Classification Search
CPC ............ A61B 18/1442; A61B 18/1445; A61B 2018/1455; A61B 2018/1452; A61B 2017/2947; A61B 2017/2948; A61B 2017/2908
See application file for complete search history.

(56) References Cited

U.S. PATENT DOCUMENTS

| | | |
|---|---|---|
| 4,174,715 A | 11/1979 | Hasson |
| 5,776,075 A | 7/1998 | Palmer |
| | (Continued) | |

*Primary Examiner* — Ronald Hupczey, Jr.
*Assistant Examiner* — Bo Ouyang

(57) ABSTRACT

A method of cutting tissue includes providing a surgical instrument including an end-effector assembly including first and second jaw members controllably movable from a first position in spaced relation relative to a third jaw member disposed therebetween to at least one second position closer to the third jaw member wherein the first, second and third jaw members cooperate to grasp tissue therebetween. Each of the first and second jaw members includes an electrically-conductive sealing plate. A cutting member is disposed on a portion of the upper surface of the third jaw member. The method also includes positioning the first, second and third jaw members about tissue, applying energy to the electrically-conductive sealing plates so that energy passes between the electrically-conductive sealing plates and through tissue to effect a tissue seal, and activating the cutting member to cut through tissue overlying the upper surface of the third jaw member.

19 Claims, 12 Drawing Sheets

(56) References Cited

U.S. PATENT DOCUMENTS

| | | | |
|---|---|---|---|
| 5,976,161 A | | 11/1999 | Kirsch et al. |
| 6,083,223 A | * | 7/2000 | Baker ................ A61B 18/1445 606/49 |
| 6,139,508 A | | 10/2000 | Simpson et al. |
| 8,241,282 B2 | * | 8/2012 | Unger ................ A61B 18/1445 606/45 |
| 9,237,900 B2 | * | 1/2016 | Boudreaux .......... A61B 17/282 |
| 2005/0124912 A1 | | 6/2005 | Griego et al. |
| 2005/0182426 A1 | | 8/2005 | Adams et al. |
| 2005/0267529 A1 | | 12/2005 | Crockett et al. |
| 2007/0244510 A1 | | 10/2007 | Weizman et al. |
| 2010/0016883 A1 | | 1/2010 | Christoudias |
| 2010/0137854 A1 | * | 6/2010 | Hosier ................... A61B 18/12 606/33 |
| 2010/0185196 A1 | * | 7/2010 | Sakao ................ A61B 18/1445 606/51 |
| 2011/0077668 A1 | | 3/2011 | Gordon et al. |
| 2012/0083783 A1 | * | 4/2012 | Davison ............. A61B 18/1445 606/45 |
| 2012/0239080 A1 | | 9/2012 | Fan |
| 2013/0085494 A1 | | 4/2013 | Weisenburgh, II et al. |

* cited by examiner

SURGICAL INSTRUMENT WITH END-EFFECTOR ASSEMBLY INCLUDING THREE JAW MEMBERS AND METHODS OF CUTTING TISSUE USING SAME

CROSS REFERENCE TO RELATED APPLICATION

The present application claims the benefit of and priority to U.S. Provisional Application Ser. No. 61/910,634, filed on Dec. 2, 2013, the entire contents of which are incorporated herein by reference.

BACKGROUND

1. Technical Field

The present disclosure relates to surgical instruments, such as electrosurgical and ultrasonic devices, and methods for cutting tissue. More particularly, the present disclosure relates to surgical instruments that include an end-effector assembly including first and second jaw members capable of applying a combination of mechanical clamping pressure and energy to effectively seal tissue and a third jaw member disposed between the first and second jaw members configured to selectively sever tissue between the sealed tissue areas.

2. Discussion of Related Art

Electrosurgical and ultrasonic devices have become widely used by surgeons. Electrosurgery involves the application of thermal and/or electrical energy to cut, dissect, ablate, coagulate, cauterize, seal or otherwise treat biological tissue during a surgical procedure. Electrosurgery is typically performed using an electrosurgical generator operable to output energy and a handpiece including a surgical instrument (e.g., end effector) adapted to transmit energy to a tissue site during electrosurgical procedures. Electrosurgery can be performed using either a monopolar or a bipolar instrument.

The basic purpose of both monopolar and bipolar electrosurgery is to produce heat to achieve the desired tissue/clinical effect. In monopolar electrosurgery, devices use an instrument with a single, active electrode to deliver energy from an electrosurgical generator to tissue, and a patient return electrode or pad that is attached externally to the patient (e.g., a plate positioned on the patient's thigh or back) as the means to complete the electrical circuit between the electrosurgical generator and the patient. When the electrosurgical energy is applied, the energy travels from the active electrode, to the surgical site, through the patient and to the return electrode.

In bipolar electrosurgery, both the active electrode and return electrode functions are performed at the site of surgery. Bipolar electrosurgical devices include two electrodes that are located in proximity to one another for the application of current between their surfaces. Bipolar electrosurgical current travels from one electrode, through the intervening tissue to the other electrode to complete the electrical circuit. Bipolar instruments generally include end-effectors, such as grippers, cutters, forceps, dissectors and the like.

Forceps utilize mechanical action to constrict, grasp, dissect and/or clamp tissue. By utilizing an electrosurgical forceps, a surgeon can utilize both mechanical clamping action and electrosurgical energy to effect hemostasis by heating the tissue and blood vessels to cauterize, coagulate/desiccate, seal and/or divide tissue. Bipolar electrosurgical forceps utilize two generally opposing electrodes that are operably associated with the inner opposing surfaces of the end effectors and that are both electrically coupled to an electrosurgical generator. In bipolar forceps, the end-effector assembly generally includes opposing jaw assemblies pivotably mounted with respect to one another. In a bipolar configuration, only the tissue grasped between the jaw assemblies is included in the electrical circuit. Because the return function is performed by one jaw assembly of the forceps, no patient return electrode is needed.

By utilizing an electrosurgical forceps, a surgeon can cauterize, coagulate/desiccate and/or seal tissue and/or simply reduce or slow bleeding by controlling the intensity, frequency and duration of the electrosurgical energy applied through the jaw assemblies to the tissue. During the sealing process, mechanical factors such as the pressure applied between opposing jaw assemblies and the gap distance between the electrically-conductive tissue-contacting surfaces (electrodes) of the jaw assemblies play a role in determining the resulting thickness of the sealed tissue and effectiveness of the seal.

A variety of types of end-effector assemblies have been employed for various types of surgery, e.g., electrosurgery using a variety of types of monopolar and bipolar electrosurgical instruments.

SUMMARY

A continuing need exists for a reliable surgical instrument that assists in gripping, manipulating and holding tissue prior to and during activation and dividing of the tissue. A need exists for surgical instruments with an end-effector assembly suitable for use with a variety of energy sources.

According to an aspect of the present disclosure, a method of cutting tissue is provided. The method includes the initial step of providing a surgical instrument for sealing tissue. The surgical instrument includes an end-effector assembly having first and second jaw members controllably movable from a first position in spaced relation relative to a third jaw member disposed therebetween to at least one second position closer to the third jaw member wherein the first, second and third jaw members cooperate to grasp tissue therebetween. Each of the first and second jaw members includes an electrically-conductive sealing plate connectable to an energy source and configured to apply energy through tissue held therebetween. A cutting member is disposed on a portion of the upper surface of the third jaw member. The method also includes the steps of positioning the first, second and third jaw members about tissue, applying energy to the electrically-conductive sealing plates so that energy passes between the electrically-conductive sealing plates and through tissue to effect a tissue seal, and activating the cutting member to cut through tissue overlying the upper surface of the third jaw member.

According to another aspect of the present disclosure, a method of cutting tissue is provided and includes the initial step of providing a surgical instrument for sealing tissue. The surgical instrument includes an elongated shaft having an end-effector assembly at a distal end thereof. The end-effector assembly includes first and second jaw members controllably movable from a first position in spaced relation relative to a third jaw member disposed therebetween to at least one second position closer to the third jaw member wherein the first, second and third jaw members cooperate to grasp tissue therebetween. Each of the first and second jaw members includes an electrically-conductive sealing plate connectable to an energy source and configured to apply energy through tissue held therebetween. The third jaw member includes a blade channel defined therein configured to slideably receive a blade including a cutting edge at a distal end thereof. The blade is selectively movable from a first configuration wherein the cutting edge is recessed within the elongated shaft to a second configuration wherein a portion of the blade is disposed within the blade channel. The method also includes the steps of positioning the first, second and third jaw members about tissue, applying energy to the electrically-conductive sealing plates so that energy passes between the electrically-conductive sealing plates and through tissue to effect a tissue seal, and moving the blade in at least one direction such that the portion of the blade rides within the blade channel and extends the cutting edge into and through tissue overlying the upper surface of the third jaw member.

BRIEF DESCRIPTION OF THE DRAWINGS

Objects and features of the presently-disclosed surgical instruments and end-effector assemblies including three jaw members for use in surgical instruments to grasp, seal, and/or cut tissue will become apparent to those of ordinary skill in the art when descriptions of various embodiments thereof are read with reference to the accompanying drawings, of which.

DETAILED DESCRIPTION

Figure 1:
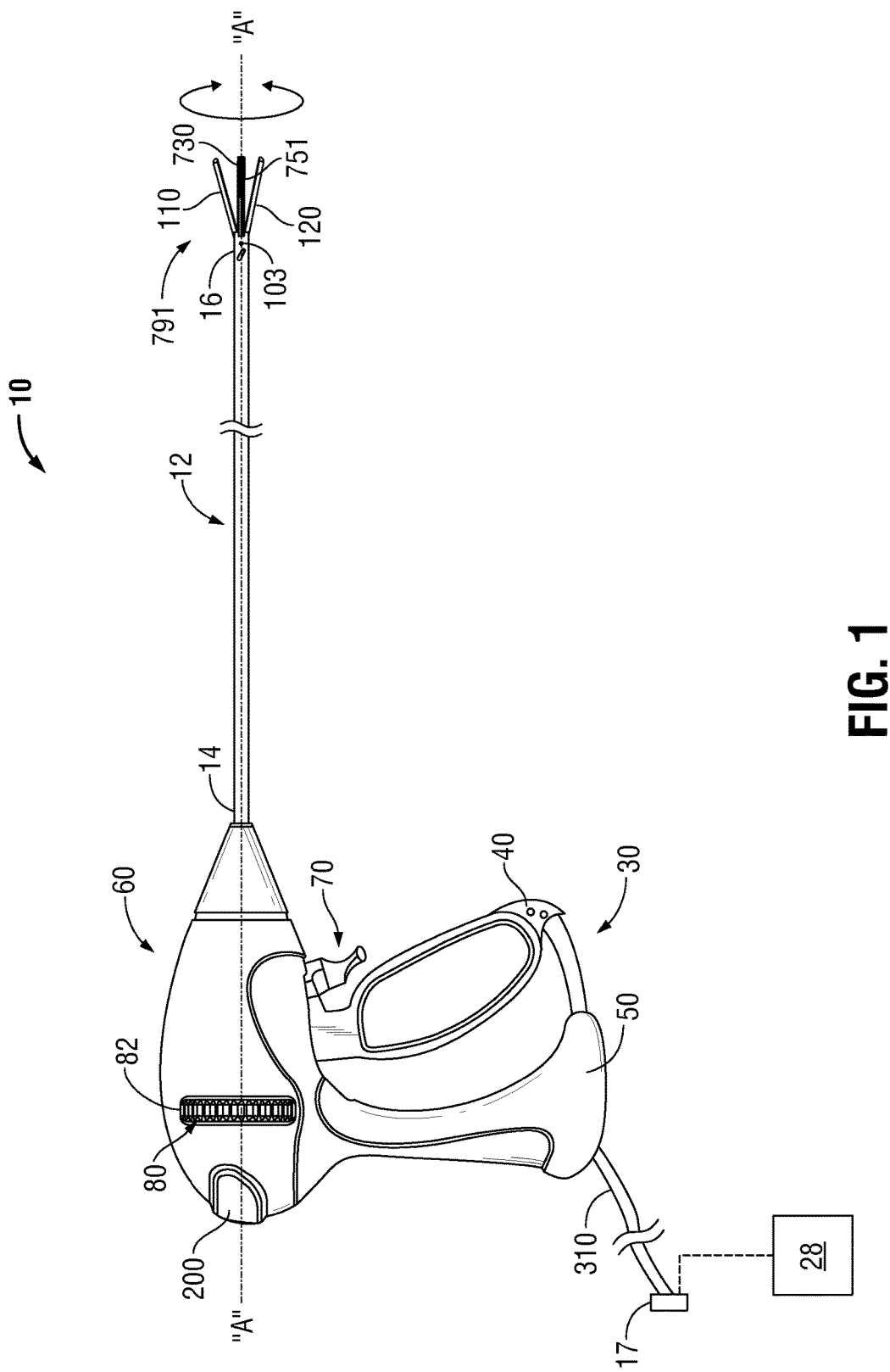
FIG. 1 is a right, side view of a surgical instrument showing a housing, a rotatable member, a shaft, and an end-effector assembly including three jaw members in accordance with an embodiment of the present disclosure.

Hereinafter, embodiments of surgical instruments and end-effector assemblies including three jaw members for use in surgical instruments to grasp, seal, and/or cut tissue of the present disclosure, and methods of cutting tissue of the present disclosure are described with reference to the accompanying drawings. Like reference numerals may refer to similar or identical elements throughout the description of the figures. As shown in the drawings and as used in this description, and as is traditional when referring to relative positioning on an object, the term "proximal" refers to that portion of the apparatus, or component thereof, closer to the user and the term "distal" refers to that portion of the apparatus, or component thereof, farther from the user.

This description may use the phrases "in an embodiment," "in embodiments," "in some embodiments," or "in other embodiments," which may each refer to one or more of the same or different embodiments in accordance with the present disclosure.

Various embodiments of the present disclosure provide surgical instruments suitable for sealing, cauterizing, coagulating/desiccating, and/or cutting vessels and vascular tissue. Embodiments of the presently-disclosed surgical instruments with an end-effector assembly including three jaw members may be suitable for utilization in endoscopic surgical procedures and/or suitable for utilization in open surgical applications. Embodiments of the presently-disclosed surgical instruments may be implemented using a variety of types of energy, e.g., electrosurgical energy at radio frequencies (RF) and/or at other frequencies, ultrasonic, optical, and/or thermal energy. Embodiments of the presently-disclosed surgical instruments may be configured to be connectable to one or more energy sources, e.g., RF generators and/or ultrasonic generators.

The various embodiments disclosed herein may also be configured to work with robotic surgical systems and what is commonly referred to as "Telesurgery." Such systems employ various robotic elements to assist the surgeon in the operating theater and allow remote operation (or partial remote operation) of surgical instrumentation. Various robotic arms, gears, cams, pulleys, electric and mechanical motors, etc. may be employed for this purpose and may be designed with a robotic surgical system to assist the surgeon during the course of an operation or treatment. Such robotic systems may include, remotely steerable systems, automatically flexible surgical systems, remotely flexible surgical systems, remotely articulating surgical systems, wireless surgical systems, modular or selectively configurable remotely operated surgical systems, etc.

The robotic surgical systems may be employed with one or more consoles that are next to the operating theater or located in a remote location. In this instance, one team of surgeons or nurses may prep the patient for surgery and configure the robotic surgical system with one or more of the instruments disclosed herein while another surgeon (or group of surgeons) remotely control the instruments via the robotic surgical system. As can be appreciated, a highly skilled surgeon may perform multiple operations in multiple locations without leaving his/her remote console which can be both economically advantageous and a benefit to the patient or a series of patients.

The robotic arms of the surgical system are typically coupled to a pair of master handles by a controller. The handles can be moved by the surgeon to produce a corresponding movement of the working ends of any type of surgical instrument (e.g., end effectors, graspers, knifes, scissors, etc.) which may complement the use of one or more of the embodiments described herein. In various embodiments disclosed herein, an end-effector assembly including three jaw members may be coupled to a pair of master handles by a controller. The movement of the master handles may be scaled so that the working ends have a corresponding movement that is different, smaller or larger, than the movement performed by the operating hands of the surgeon. The scale factor or gearing ratio may be adjustable so that the operator can control the resolution of the working ends of the surgical instrument(s).

The master handles may include various sensors to provide feedback to the surgeon relating to various tissue parameters or conditions, e.g., tissue resistance due to manipulation, cutting or otherwise treating, pressure by the three jaw members onto the tissue, tissue temperature, tissue impedance, etc. As can be appreciated, such sensors provide the surgeon with enhanced tactile feedback simulating actual operating conditions. The master handles may also include a variety of different actuators for delicate tissue manipulation or treatment further enhancing the surgeon's ability to mimic actual operating conditions.

In FIG. 1, an embodiment of a surgical instrument 10 is shown for use with various surgical procedures, e.g., endoscopic surgical procedures. Surgical instrument 10 generally includes a housing 60, a handle assembly 30, a rotatable assembly 80, a trigger assembly 70, and an end-effector assembly 791 that mutually cooperate to grasp, seal and/or divide tissue (e.g., tissue "T" shown in FIG. 5), e.g., tubular vessels and vascular tissue. End-effector assembly 791 includes a first jaw member 110, a second jaw member 120, and a third jaw member 730 disposed between the first and second jaw members 110 and 120, respectively, which are configured to be controllably movable, e.g., to grasp and/or seal tissue.

Figure 4:
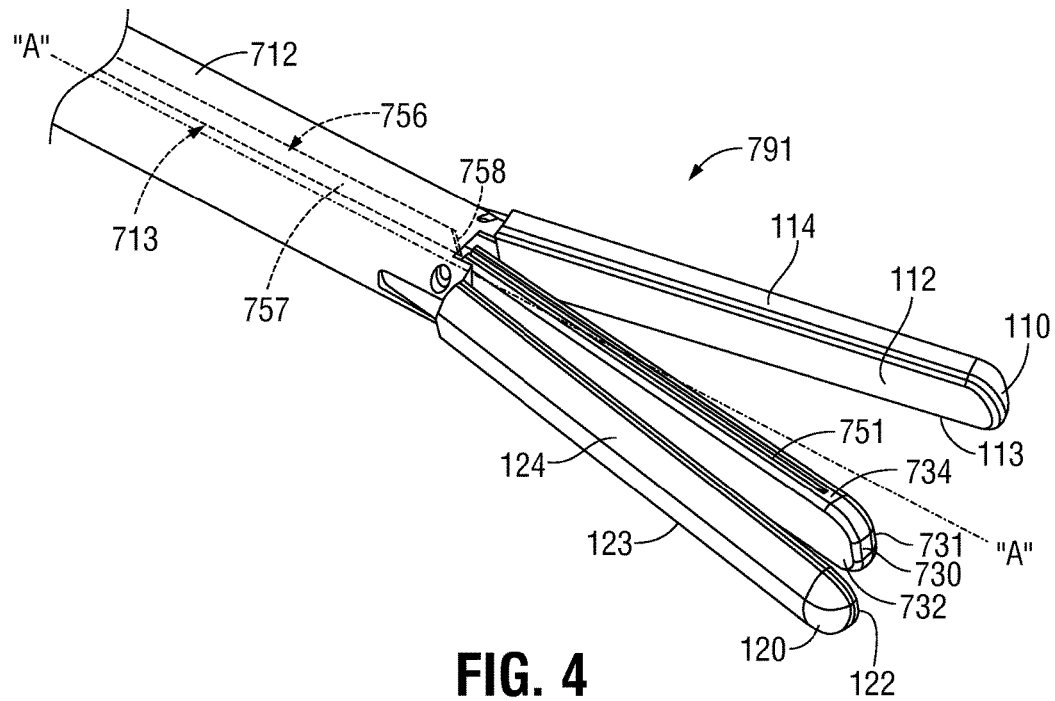
FIG. 4 is an enlarged, perspective view of the end-effector assembly of FIG. 3 showing the third jaw member disposed downwardly at a first angle in accordance with an embodiment of the present disclosure.
Figure 5:
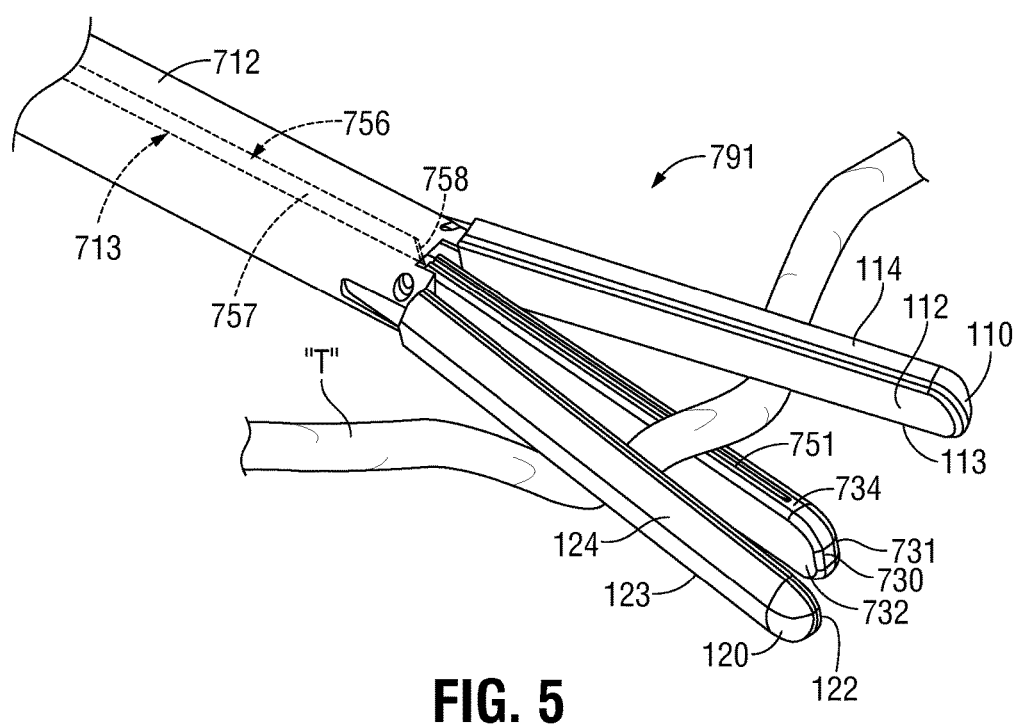
FIG. 5 is an enlarged, perspective view of the end-effector assembly of FIG. 4 shown with tissue disposed below the lower surfaces of the first and second jaw members and tissue overlying a channel defined in the upper surface of the third jaw member in accordance with an embodiment of the present disclosure.
Figure 7:
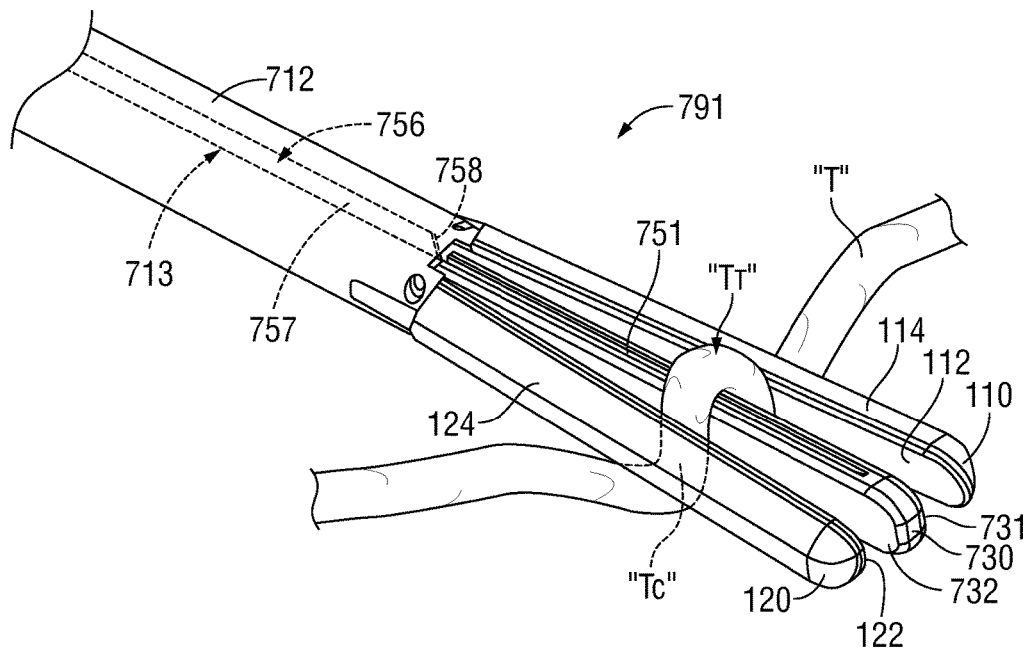
FIG. 7 is an enlarged, perspective view of the end-effector assembly of FIG. 6 showing the first and second jaw members in a closed configuration with tissue in compression disposed between the electrically-conductive tissue-engaging surfaces of the third jaw member and the electrically-conductive tissue-engaging surfaces of the first and second jaw members, respectively, and tissue in tension overlying the channel defined in the upper surface of the third jaw member, in accordance with an embodiment of the present disclosure.
Figure 8:
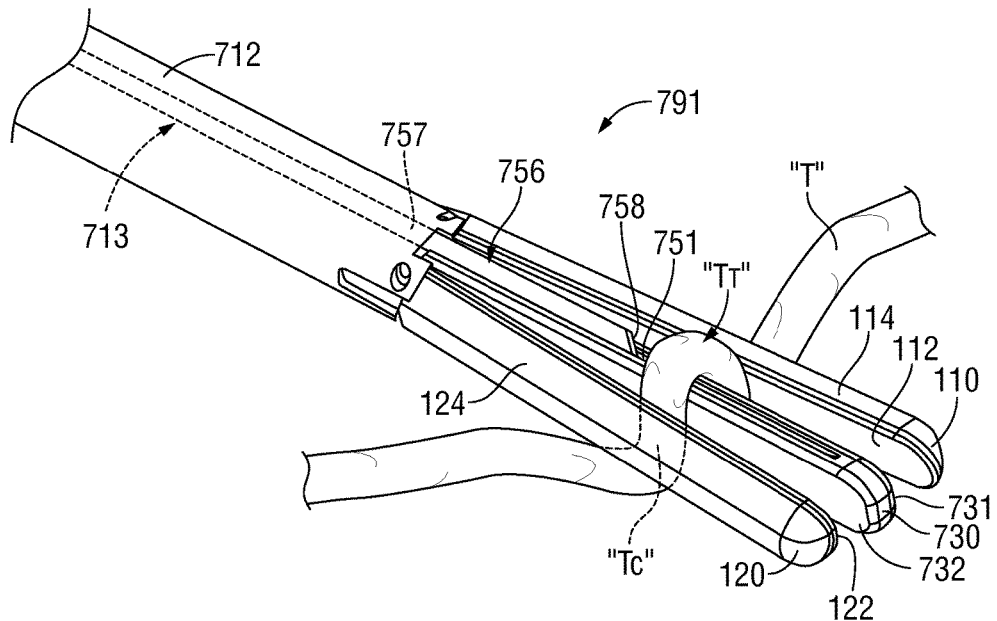
FIG. 8 is an enlarged, perspective view of the end-effector assembly of FIG. 7 showing the first and second jaw members in a closed configuration with sealed tissue in compression disposed between the electrically-conductive tissue-engaging surfaces of the third jaw member and the electrically-conductive surfaces of the first and second jaw members, respectively, shown with the knife partially extended along a portion of the upper surface of the third jaw member, in accordance with an embodiment of the present disclosure.

First and second jaw members 110 and 120 are configured to be controllably movable relative to one another and/or relative to the third jaw member 730, e.g., to control the amount of compression applied to tissue (e.g., tissue in compression "$T_C$" shown in FIGS. 7 and 8). In some embodiments, the instrument 10 is configured to provide a user capability to controllably move the first and second jaw members 110 and 120 laterally towards the third jaw member 730 to progressively tension tissue (e.g., tissue in tension "$T_T$" shown in FIGS. 7 and 8) overlying the upper surface 734 of the third jaw member 730. As best seen in FIGS. 4 and 5, the third jaw member 730 is movable from a first configuration, wherein the first, second and third jaw members are disposed in vertical alignment relative to one another (e.g., an upper surface 734 of the third jaw member 730 is substantially coplanar with the upper surfaces 114 and 124 of the first and second jaw members 110 and 120, respectively), to a second configuration, wherein the upper surface 734 of the third jaw member 730 is disposed at an angle, e.g., relative to a plane defined by the upper surfaces 114 and 124 of the first and second jaw members 110 and 120, respectively.

Surgical instrument 10 generally includes an elongated shaft 12 defining a longitudinal axis "A-A". Shaft 12 supports movement of other components therethrough, e.g., to impart movement to the first, second and third jaw members 110, 120 and 730, respectively. In some embodiments, the trigger assembly 70 is operatively coupled to the end-effector assembly 791, e.g., to allow the surgeon to change the position and/or orientation of the third jaw member 730.

Although FIG. 1 depicts a surgical instrument 10 for use in connection with endoscopic surgical procedures, the teachings of the present disclosure may also apply to more traditional open surgical procedures. For the purposes herein, the device 10 is described in terms of an endoscopic instrument; however, an open version of the device may also include the same or similar operating components and features as described below.

Figure 3:
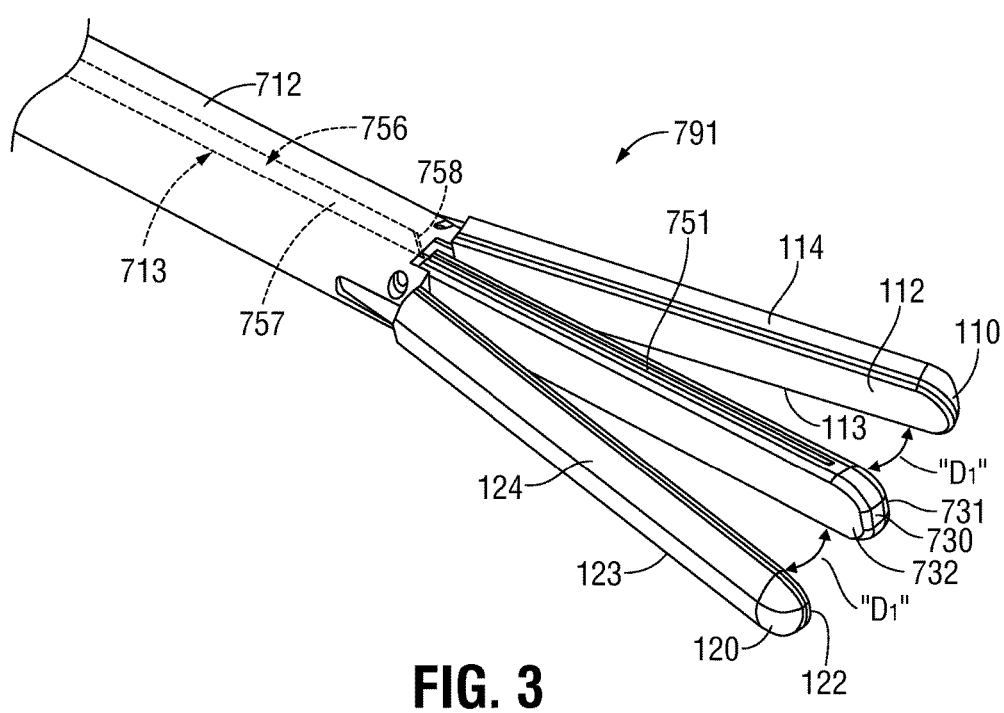
FIG. 3 is an enlarged, perspective view of the end-effector assembly of FIG. 2 disposed in an open configuration, wherein the first and second jaw members are spaced apart from the third jaw member disposed therebetween, showing electrically-conductive tissue-engaging surfaces associated with the first, second and third jaw members, in accordance with an embodiment of the present disclosure.

In some embodiments, as shown in FIG. 1, first jaw member 110 and the second jaw member 120 are pivotably connected about a pivot pin 103 and controllably movable relative to one another and/or relative to the third jaw member 730, e.g., pivotably movable about the pivot pin 103, in a curvilinear direction "$D_1$" as shown in FIG. 3. First jaw member 110, the second jaw member 120, and/or the third jaw member 730 may be curved at various angles to facilitate manipulation of tissue and/or to provide enhanced line-of-sight for accessing targeted tissues. The first, second, and third jaw members 110, 120, and 730, respectively, may be formed from any suitable material or combination of materials by any suitable process, e.g., machining, stamping, electrical discharge machining (EDM), forging, casting, injection molding, metal injection molding (MIM), and/or fineblanking. End-effector assembly 791 may include one or more electrically-insulative elements to electrically isolate the first jaw member 110 from the second jaw member 120. End-effector assembly 791 may additionally, or alternatively, include one or more electrically-insulative bushings to electrically isolate the third jaw member 730 from the first jaw member 110 and/or the second jaw member 120.

End-effector assembly 791 may include one or more electrically-conductive tissue-engaging surfaces (also referred to herein as "sealing plates") coupled to, or otherwise disposed in association with, the first, second and/or third jaw member 110, 120 and/or 730, respectively. In some embodiments, as shown in FIGS. 2 through 9, end-effector assembly 791 includes first and second electrically-conductive tissue-engaging surfaces 112 and 122, respectively, wherein the first electrically-conductive tissue-engaging surface 112 is coupled to, or otherwise disposed in association with, the first jaw member 110, and the second electrically-conductive tissue-engaging surface 122 is coupled to, or otherwise disposed in association with, the second jaw member 120. End-effector assembly 791 may include electrically-insulative members configured to electrically isolate, at least in part, the first and second electrically-conductive tissue-engaging surfaces 112 and 122 (also referred to herein as "first and second sealing plates 112 and 122") from the first and second jaw members 110 and 120, respectively. In some embodiments, the first and second sealing plates 112 and 122 may be integrally formed with the first and second jaw members 110 and 120, respectively. End-effector assembly 791 may additionally, or alternatively, include electrically-conductive tissue-engaging surfaces coupled to, or otherwise disposed in association with, the third jaw member 730.

In some embodiments, as shown in FIGS. 2 through 9, the end-effector assembly 791 includes a first sealing plate 112 associated with the first jaw member 110, a second sealing plate 122 associated with the second jaw member 120, and third and fourth sealing plates 731 and 732 associated with the third jaw member 730, wherein the first and third sealing plates 112 and 731, respectively, are disposed in opposing relation to one another, and wherein the second and fourth sealing plates 122 and 732, respectively, are disposed in opposing relation to one another. In some embodiments, the end-effector assembly 791 may be configured to allow the first, second, third and fourth sealing plates 112, 122, 731 and 732 to be separately activated, and/or activated in pairs (e.g., first and third sealing plates 112 and 731 and/or second and fourth sealing plates 122 and 732).

As shown in FIG. 1, the shaft 12 includes a distal end 16 configured to mechanically engage the end-effector assembly 1291. In some embodiments, the end-effector assembly 791 is selectively and releaseably engageable with the distal end 16 of the shaft 12. In some embodiments, the shaft 12 includes an inner shaft member slidingly disposed within an outer shaft member and operable by a drive assembly (not shown). The proximal end 14 of the shaft 12 is received within the housing 60 and examples of connections relating thereto, and examples of drive assembly embodiments of the surgical instrument 10, are described in commonly assigned U.S. Pat. No. 7,150,097 entitled "METHOD OF MANUFACTURING JAW ASSEMBLY FOR VESSEL SEALER AND DIVIDER," commonly assigned U.S. Pat. No. 7,156,846 entitled "VESSEL SEALER AND DIVIDER FOR USE WITH SMALL TROCARS AND CANNULAS," commonly assigned U.S. Pat. No. 7,597,693 entitled "VESSEL SEALER AND DIVIDER FOR USE WITH SMALL TROCARS AND CANNULAS," and commonly assigned U.S. Pat. No. 7,771,425 entitled "VESSEL SEALER AND DIVIDER HAVING A VARIABLE JAW CLAMPING MECHANISM."

Surgical instrument 10 includes a cable 310. Cable 310 may be formed from a suitable flexible, semi-rigid or rigid cable, and may connect directly to an energy source 28, e.g., an ultrasonic and/or electrosurgical power generating source. In some embodiments, the cable 310 connects the surgical instrument 10 to a connector 17, which further operably connects the instrument 10 to the energy source 28. Cable 310 may be internally divided into one or more cable leads (not shown) each of which transmits energy through its respective feed path to the end-effector assembly 1291. In some embodiments, cable 310 may include optical fiber.

Energy source 28 may be any generator suitable for use with surgical devices, and may be configured to provide various frequencies of electrosurgical energy, optical energy, and/or ultrasound. Examples of electrosurgical generators that may be suitable for use as a source of electrosurgical energy are commercially available under the trademarks FORCE EZ™, FORCE FX™, and FORCE TRIAD™ offered by Covidien Surgical Solutions of Boulder, Colo.

Surgical instrument 10 may alternatively be configured as a wireless device or battery-powered.

As shown in FIG. 1, the end-effector assembly 791 is rotatable about a longitudinal axis "A-A" through rotation, either manually or otherwise, of the rotatable assembly 80. Rotatable assembly 80 generally includes two halves (not shown), which, when assembled about the shaft 12, form a generally circular rotatable member 82. Rotatable assembly 80, or portions thereof, may be configured to house a drive assembly (not shown) or components thereof. Examples of rotatable assembly embodiments and drive assembly embodiments of the surgical instrument 10 are described in the above-mentioned, commonly-assigned U.S. Pat. Nos. 7,150,097, 7,156,846, 7,597,693 and 7,771,425.

Handle assembly 30 includes a fixed handle 50 and a movable handle 40. In some embodiments, the fixed handle 50 is integrally associated with the housing 60, and the movable handle 40 is selectively movable relative to the fixed handle 50. Movable handle 40 of the handle assembly 30 is ultimately connected to the drive assembly (not shown). As can be appreciated, applying force to move the movable handle 40 toward the fixed handle 50 pulls a drive element (e.g., inner shaft member 180) proximally to impart movement to the first and second jaw members 110 and 120 from an open position, wherein the first and second jaw members 110 and 120 are disposed in spaced relation relative to the third jaw member 730, to a clamping or closed position, wherein the first, second and third jaw members 110, 120 and 730 cooperate to grasp tissue therebetween. Examples of handle assembly embodiments of the surgical instrument 10 are described in the above-mentioned, commonly-assigned U.S. Pat. Nos. 7,150,097, 7,156,846, 7,597, 693 and 7,771,425.

Surgical instrument 10 includes a switch 200 configured to permit the user to selectively activate the instrument 10 in a variety of different orientations, i.e., multi-oriented activation. As can be appreciated, this simplifies activation. When the switch 200 is depressed, energy is transferred through one or more pathways, e.g., electrical leads (not shown) and/or optical fiber (not shown), to the first and second jaw members 110 and 120. Additionally, or alternatively, when switch 200 is depressed, energy may be transferred through one or more pathways, e.g., electrical leads (not shown) and/or optical fiber (not shown), to the third jaw member 730. Although FIG. 1 depicts the switch 200 disposed at the proximal end of the housing assembly 60, switch 200 may be disposed on another part of the instrument 10 (e.g., the fixed handle 50, rotatable member 82, etc.) or another location on the housing assembly 60.

FIGS. 2 through 9 show a knife 756 operatively coupled to a shaft 712 (similar to the elongated shaft 12 shown in FIG. 1) and an end-effector assembly 791 disposed at the distal end of the shaft 712. Knife 756 includes a knife bar 757 and a knife blade 758 disposed at the distal end of the knife bar 757. Third jaw member 730 includes a channel 751 defined along the length of the upper surface 734, or portion thereof, configured to slideably receive a portion of the knife 756, e.g., a portion including the bottom edge of the knife bar 757. Channel 751 may have any suitable dimensions, e.g., length, width, and depth.

Figure 2:
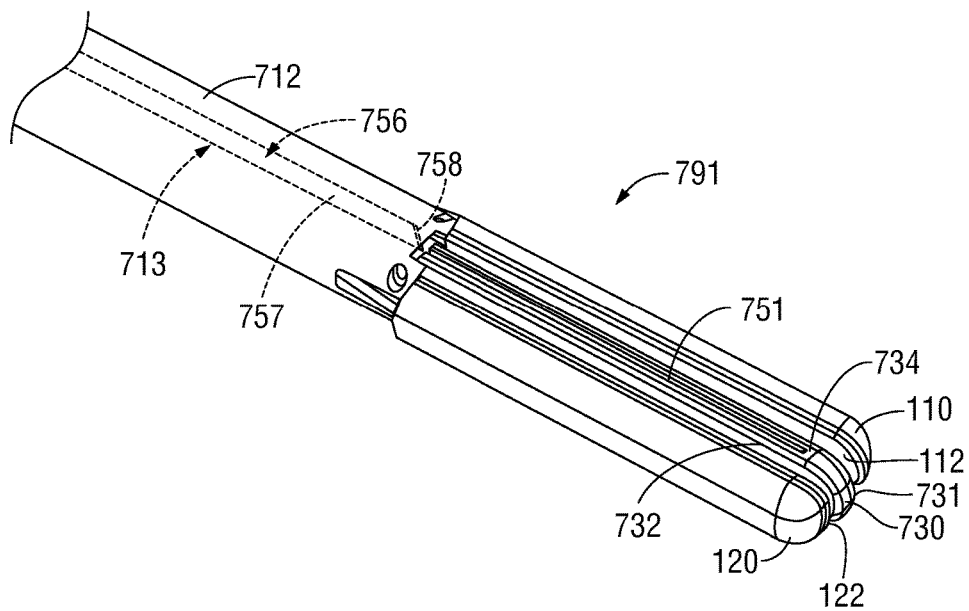
FIG. 2 is an enlarged, perspective view of a portion of a surgical instrument including an elongated shaft, an end-effector assembly including first, second and third jaw members, and a knife including a knife blade disposed within the distal end portion of the shaft in accordance with an embodiment the present disclosure.

FIG. 2 shows the end-effector assembly 791 disposed in a closed configuration, wherein the first and second jaw members 110 and 120 are positioned proximate to the third jaw member 730 disposed therebetween. In FIG. 3, the end-effector assembly 791 is shown disposed in an open configuration, wherein the first and second jaw members 110 and 120 are spaced apart from the third jaw member 730 disposed therebetween. First and second jaw members 110 and 120 are movable with respect to one another and/or with respect to the third jaw member 730, e.g., along a curvilinear direction "D1" (FIG. 3), from an open configuration wherein the first and second jaw members 110 and 120 are disposed in spaced relation relative to the third jaw member 730, to a clamping or closed position, wherein the first, second and third jaw members 110, 120 and 730 cooperate to grasp tissue (e.g., tissue "T" shown in FIG. 7) therebetween. When the end-effector assembly 791 is disposed in an open configuration, e.g., as shown in FIG. 3, the first and second electrically-conductive tissue-engaging surfaces 731 and 732 of the third jaw member 730 are spaced apart from the first and second electrically-conductive tissue-engaging surfaces 112 and 122 of the first and second jaw members 110 and 120, respectively.

Shaft 712 supports movement of other components therethrough, e.g., to impart movement to the knife 756 and the first, second and third jaw members 110, 120 and 730, respectively. In some embodiments, as shown in FIGS. 2 through 9, shaft 712 includes a longitudinally-extending channel 713 defined therethrough. The knife bar 757 is configured to be slideably translatable through the channel 713 to allow for selective advancement of the knife blade 758. In some embodiments, the end-effector assembly 791 may be configured to prevent axial translation of the knife bar 757 when the upper surface 734 of the third jaw member 730 is disposed below a plane defined by the upper surfaces 114 and 124 of the first and second jaw members 110 and 120, respectively.

FIG. 4 shows the end-effector assembly 791 disposed in an open configuration wherein the third jaw member 730 is slanted downward at a first angle, e.g., relative to a longitudinal axis "A-A" defined by the shaft 712 and/or relative to a plane defined by the upper surfaces 114 and 124 of the first and second jaw members 110 and 120, respectively. In some embodiments, the first angle may be an acute angle, e.g., an angle that measures between 0 degrees and 90 degrees. When the third jaw member 730 is slanted downward, the distal end of the third jaw member 730 is positioned offset from the longitudinal axis "A-A" defined by the shaft 712, e.g., to provide the surgeon with the capability to position tissue (e.g., tissue "T" shown in FIG. 5) over the upper surface 734 of the third jaw member 730.

FIG. 5 shows the end-effector assembly 791 positioned with respect to tissue "T", e.g., tubular vessel, wherein portions of tissue "T" are disposed below the lower surfaces 113 and 123 of the first and second jaw members 110 and 120, respectively, and a portion of tissue "T" is disposed above the upper surface 734 of the third jaw member 730.

Figure 6:
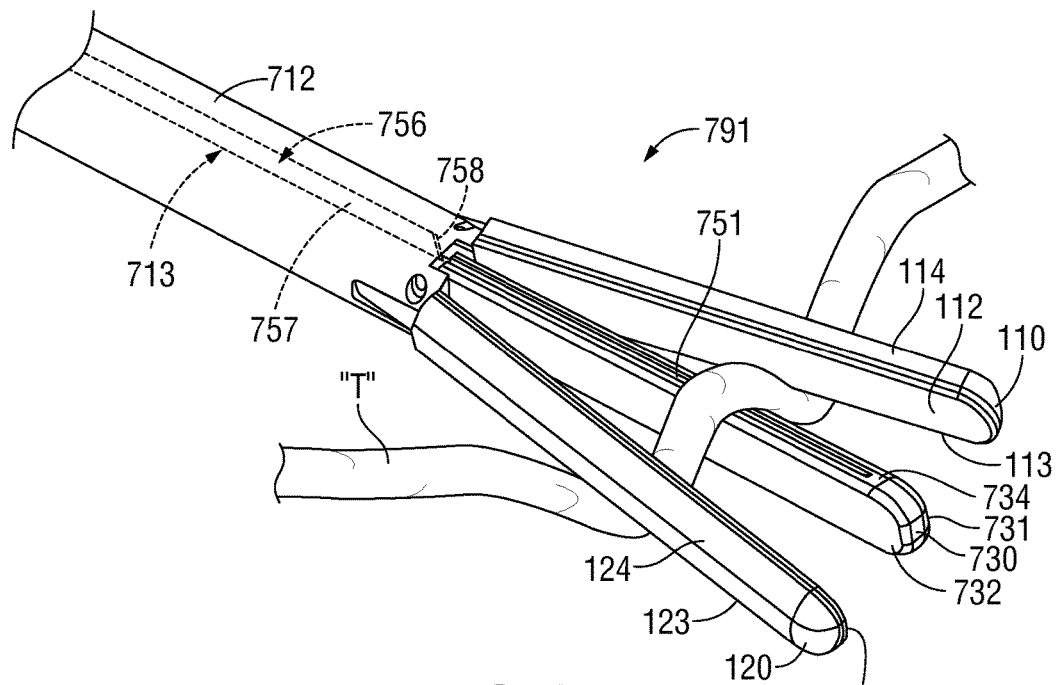
FIG. 6 is an enlarged, perspective view of the end-effector assembly of FIG. 5, showing the first, second, and third jaw members disposed in vertical alignment relative to one another, wherein the upper surfaces of the first and second jaw members are substantially coplanar with the upper surface of the third jaw member, in accordance with an embodiment of the present disclosure.

FIG. 6 shows the end-effector assembly 791 disposed in a configuration wherein the first, second, and third jaw members 110, 120 and 730, respectively, are disposed in vertical alignment relative to one another, wherein the upper surfaces 114 and 124 of the first and second jaw members 110 and 120, respectively, are substantially coplanar with the upper surface 734 of the third jaw member 730.

In FIG. 7, the end-effector assembly 791 is shown with the first, second and third jaw members 110, 120 and 730 in a closed configuration, e.g., after tissue sealing, with sealed tissue in compression "$T_C$" disposed between the first and third sealing plates 112 and 731 of the first and third jaw members 110 and 730, respectively, and the second and fourth sealing plates 122 and 732 of the second and third jaw members 120 and 730, respectively, and tissue in tension "$T_T$" disposed overlying the upper surface 734 of the third jaw member 730.

FIG. 8 shows the end-effector assembly 791 with the knife 756 in a partially extended configuration, wherein a portion the knife bar 757 is disposed within the channel 751 on the upper surface 734 of the third jaw member 730 and the knife blade 758 is positioned proximal to the tissue in tension "$T_T$" disposed overlying the upper surface 734.

Figure 9:
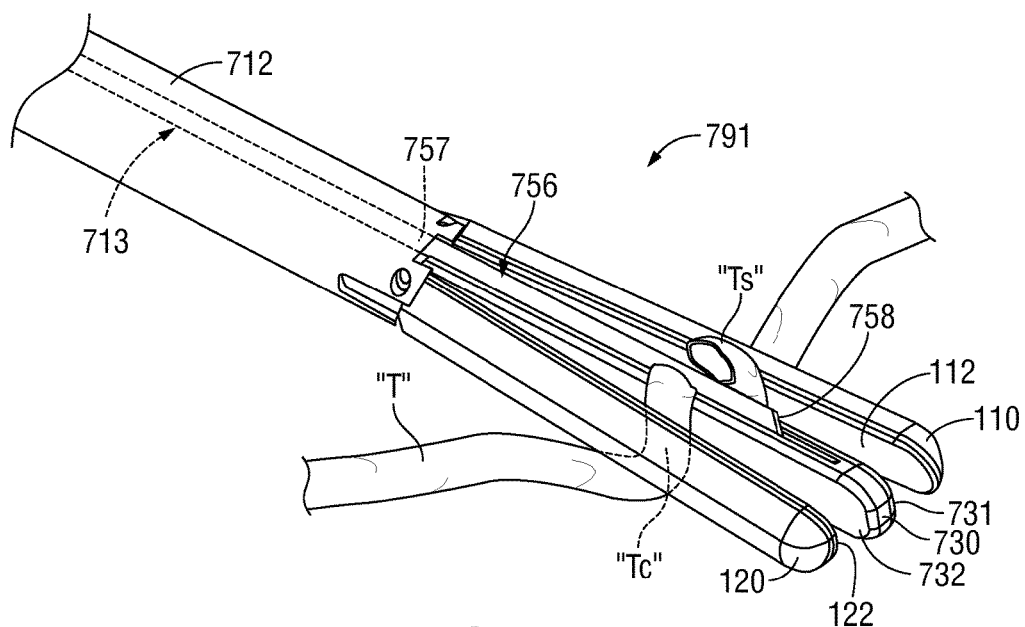
FIG. 9 is an enlarged, perspective view of the end-effector assembly of FIG. 8 showing the knife blade positioned distal to tissue severed into two portions disposed above the sealed tissue in compression in accordance with an embodiment of the present disclosure.

In FIG. 9, the end-effector assembly 791 is shown with tissue in compression "$T_C$" between the first and third sealing plates 112 and 731 of the first and third jaw members 110 and 730, respectively, and the second and fourth sealing plates 122 and 732 of the second and third jaw members 120 and 730, respectively, and with severed tissue "$T_S$" disposed above the third jaw member 730. In FIG. 9, the knife blade 758 is disposed in an extended configuration and positioned distal to the severed tissue "$T_S$" and the tissue in compression "$T_C$". The surgeon may maintain the end-effector assembly 791 in the closed configuration after tissue sealing and cutting, e.g., to view the severed tissue "$T_S$" to evaluate the integrity of the sealed tissue in compression "$T_C$".

Figure 10:
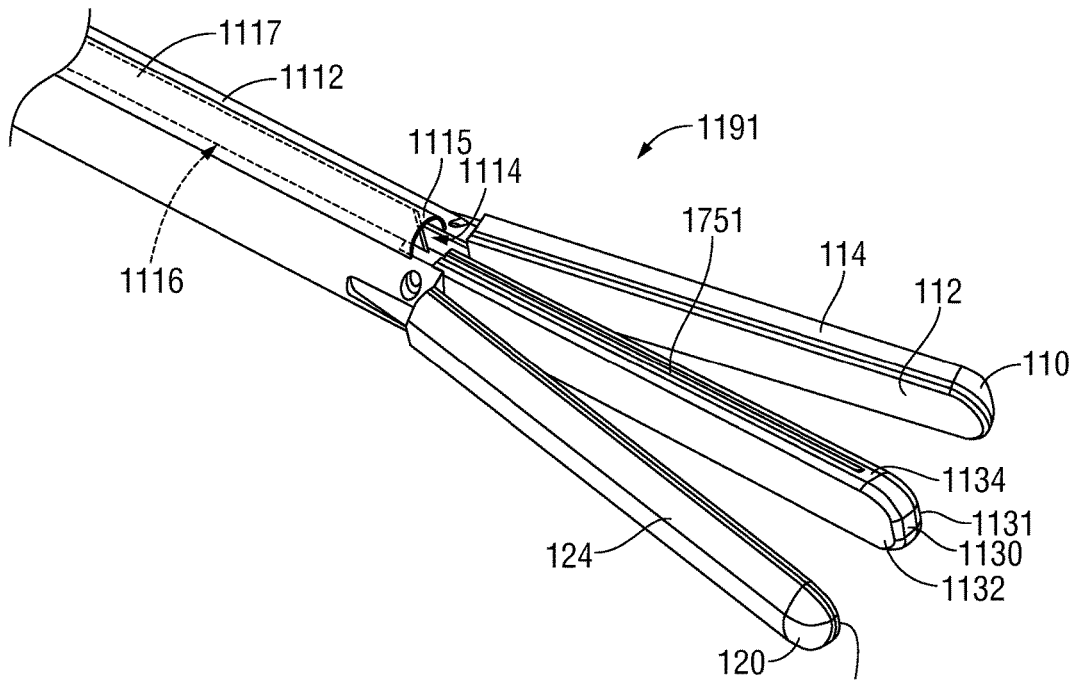
FIG. 10 is an enlarged, perspective view of an elongated shaft, a knife cover defining an interior cavity, a knife including a knife blade disposed within the interior cavity, and an end-effector assembly including first and second jaw members shown spaced apart from a third jaw member disposed therebetween in accordance with an embodiment of the present disclosure.
Figure 11:
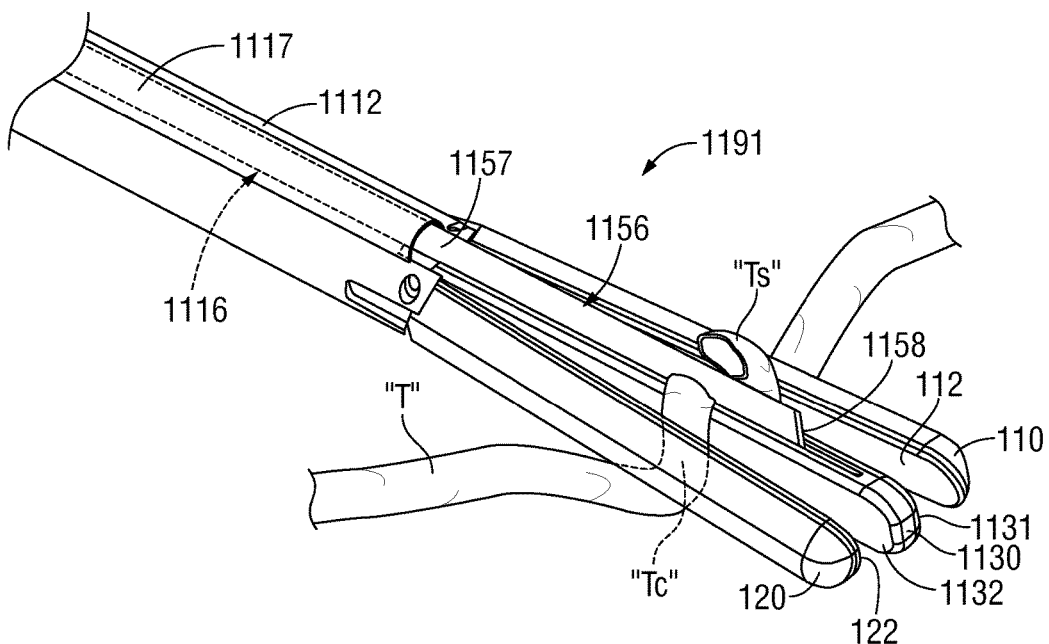
FIG. 11 is an enlarged, perspective view of the end-effector assembly of FIG. 10, showing the first and second jaw members in a closed configuration with (sealed) tissue in compression disposed between the electrically-conductive tissue-engaging surfaces of the third jaw member and the electrically-conductive surfaces of the first and second jaw members, respectively, showing the knife blade positioned distal to tissue severed into two portions disposed above the sealed tissue in compression, in accordance with an embodiment of the present disclosure.

FIGS. 10 and 11 show a portion of an elongated shaft 1112 of a surgical instrument, a knife 1156 operatively coupled to the shaft 1112, a knife cover 1117 protruding outwardly of the outer circumferential surface of the shaft 1112, and an end-effector assembly 1191 disposed at the distal end the shaft 1112. A knife cavity 1116 defined by the knife cover 1117 may be configured to receive the entire knife 1156 therein. Alternatively, the knife cavity 1116 may be configured to receive a portion, e.g., an upper portion, of the knife 1156 therein. FIG. 11 shows the knife blade 758 disposed in an extended configuration and positioned distal to the severed tissue "$T_S$" and the tissue in compression "$T_C$".

End-effector assembly 1191 includes the first and second jaw members 110 and 120 and the first and second sealing plates 112 and 122 of the end-effector assembly 791 shown in FIGS. 1 through 9, and further description of those features is omitted in the interests of brevity. End-effector assembly 1191 includes a controllably movable third jaw member 1130 disposed between the first and second jaw members 110 and 120. In some embodiments, as shown in FIGS. 10 and 11, the end-effector assembly 1191 includes third and fourth sealing plates 1131 and 1132, respectively, coupled to, or otherwise disposed in association with, the third jaw member 1130.

In FIG. 10, the end-effector assembly 1191 is shown in an open configuration wherein the first and second jaw members 110 and 120 are spaced apart from the third jaw member 1130 disposed therebetween. A channel 1751 defined along the length of the upper surface 1134 of the third jaw member 1130 is configured to slideably receive a bottom portion of the knife 1156. Channel 1751 may have any suitable dimensions, e.g., length, width, and depth. An opening 1114 at the distal end 1115 of the knife cover 1117 is disposed in communication with the knife cavity 1116 and configured to allow axial reciprocation of the knife 1156. In some embodiments, the end-effector assembly 1191 may be configured to prevent axial translation of the knife 1156 when the first, second and third jaw members 110, 120 and 1130 are not disposed in vertical alignment relative to one another, e.g., when the upper surface 1134 of the third jaw member 1130 is disposed below a plane defined by the upper surfaces 114 and 124 of the first and second jaw members 110 and 120, respectively.

Knife 1156 includes a knife bar 1157 and a knife blade 1158 disposed at the distal end of the knife bar 1157. Knife 1156 may be operatively coupled to a drive assembly (not shown) and/or a trigger assembly (e.g., trigger assembly 70 shown in FIG. 1). The drive assembly may have any suitable configuration to allow axial reciprocation of the knife 1156, e.g., to cause movement of the knife blade 1158 from a retracted position within the knife cavity 1116 to an extended position outside the knife cavity 1116. In some embodiments, the trigger assembly 70 is operatively disposed relative to a handle for selectively advancing the knife 1156 for cutting tissue along the upper surface 1134 of the third jaw member 1130.

As shown in FIG. 11, the movement of the knife blade 1158 to an extended position effects the cutting of tissue "T" in tension disposed over the upper surface 1134 of the third jaw member 1130. In some embodiments, the knife 1156 is prevented from movement, e.g., in a distal direction, when the third jaw member 1130 is disposed in an angled/slanted (downward or upward) configuration. FIG. 11 shows sealed tissue "$T_S$" in compression between the first and third sealing plates 112 and 1131 of the first and third jaw members 110 and 1130, respectively, and the second and fourth sealing plates 122 and 1132 of the second and third jaw members 120 and 1130, respectively, with cut tissue "$T_C$" disposed above the third jaw member 1130, with the knife blade 1158 positioned distal to the cut tissue "$T_C$".

FIGS. 12 through 19 show a portion of a surgical instrument including an end-effector assembly 1291. End-effector assembly 1291 includes the first and second jaw members 110 and 120 and the first and second sealing plates 112 and 122 of the end-effector assembly 791 shown in FIGS. 1 through 9, and further description of those features is omitted in the interests of brevity. End-effector assembly 1291 includes a controllably movable third jaw member 1330 disposed between the first and second jaw members 110 and 120. In some embodiments, as shown in FIGS. 12 through 18, the end-effector assembly 1291 includes third and fourth sealing plates 1331 and 1332, respectively, coupled to, or otherwise disposed in association with, the third jaw member 1330.

Figure 12:
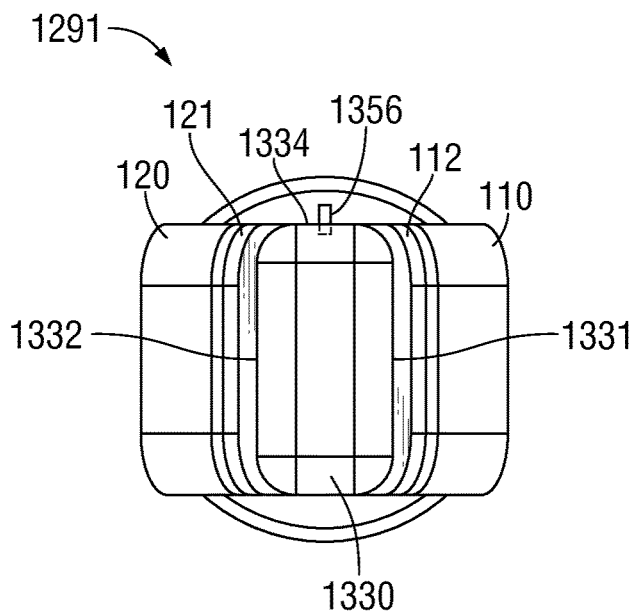
FIG. 12 is an enlarged, perspective view of the end-effector assembly of FIG. 1 disposed in a closed configuration, wherein the first and second jaw members are positioned proximate to the third jaw member disposed therebetween, showing a cutting member disposed on the upper surface the third jaw member and extending outwardly therefrom, in accordance with an embodiment of the present disclosure.

In FIG. 12, the end-effector assembly 1291 is shown with the first and second jaw members 110 and 120 in a closed configuration with the third jaw member 1330 disposed therebetween. End-effector assembly 1291 includes a cutting member 1356 disposed on the upper surface 1334 of the third jaw member 1330 and extending outwardly therefrom. End-effector assembly 1291 may include additional, fewer, or different components than shown in FIGS. 12 through 19, depending upon a particular purpose or to achieve a desired result. The shape and size of the first, second and third jaw members 110, 120 and 1330, respectively, may be varied from the configuration depicted in FIGS. 12 through 19.

In some embodiments, the cutting member 1356 is an ultrasonic member configured to treat tissue, e.g., to transect, dissect and/or coagulate tissue. The ultrasonic member may be operably coupled to an ultrasonic transducer (not shown), which may be supported within the housing of the surgical instrument and operably coupled to ultrasonic signal generator.

In some embodiments, the cutting member 1356 may have a monopolar cutting edge (not shown) configured to treat tissue, e.g., to transect, dissect and/or coagulate tissue. In such cases, the end-effector assembly 1291 may be variously configured to provide suitable electrical isolation between the monopolar cutting edge and the jaw third jaw member 1330.

FIG. 12 shows an end-effector assembly 1291 disposed in a closed configuration, wherein the first and second jaw members 110 and 120 are positioned proximate to the third jaw member 1330 disposed therebetween. A cutting member 1356 is disposed on the upper surface 1334 of the third jaw member 1330 and extends outwardly therefrom.

Figure 13:
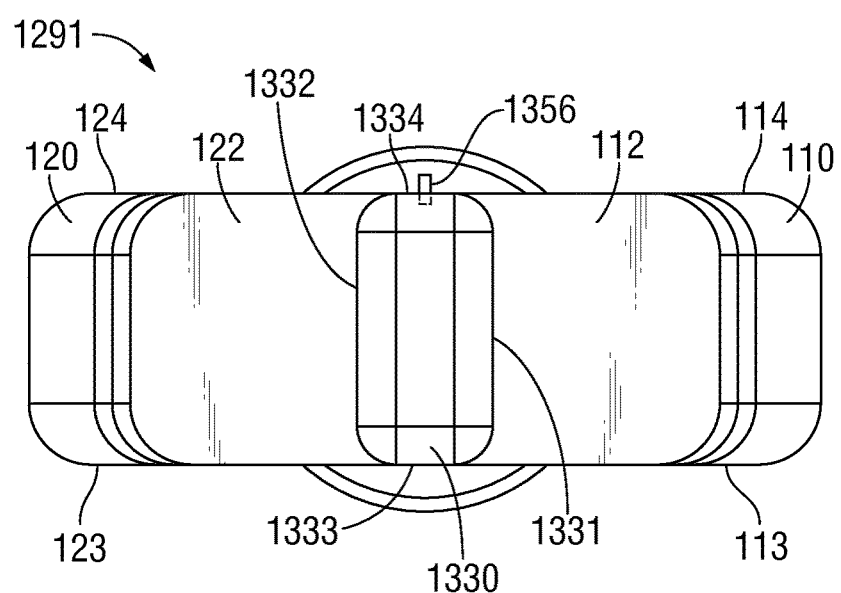
FIG. 13 is an enlarged, perspective view of the end-effector assembly of FIG. 12 disposed in an open configuration, wherein the first and second jaw members are spaced apart from the third jaw member disposed therebetween, in accordance with an embodiment of the present disclosure.

In FIG. 13, the end-effector assembly 1291 is shown in a configuration wherein the first and second jaw members 110 and 120 are disposed in spaced relation relative to the third jaw member 1330 disposed therebetween. As shown in FIG. 13, the first jaw member 110 includes an upper surface 114 and a bottom surface 113, the second jaw member 120 includes an upper surface 124 and a bottom surface 123, and the third jaw member 1330 includes an upper surface 1334 and a bottom surface 1333.

Figure 14:
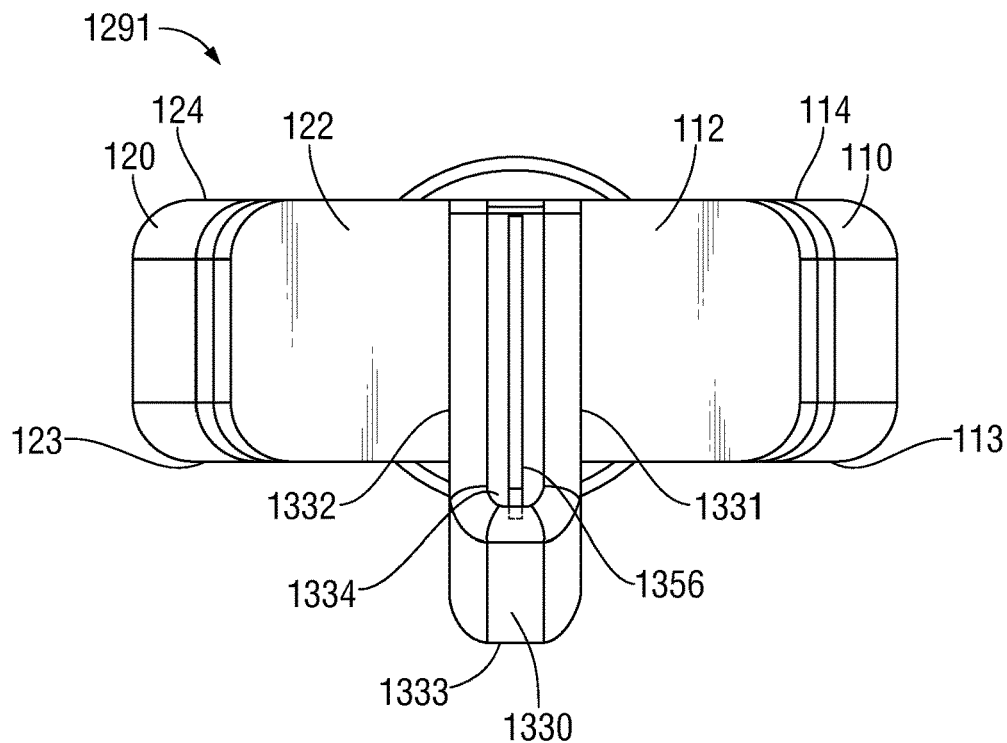
FIG. 14 is an enlarged, perspective view of the end-effector assembly of FIG. 13 showing the third jaw member disposed downwardly at a first angle in accordance with an embodiment of the present disclosure.
Figure 15:
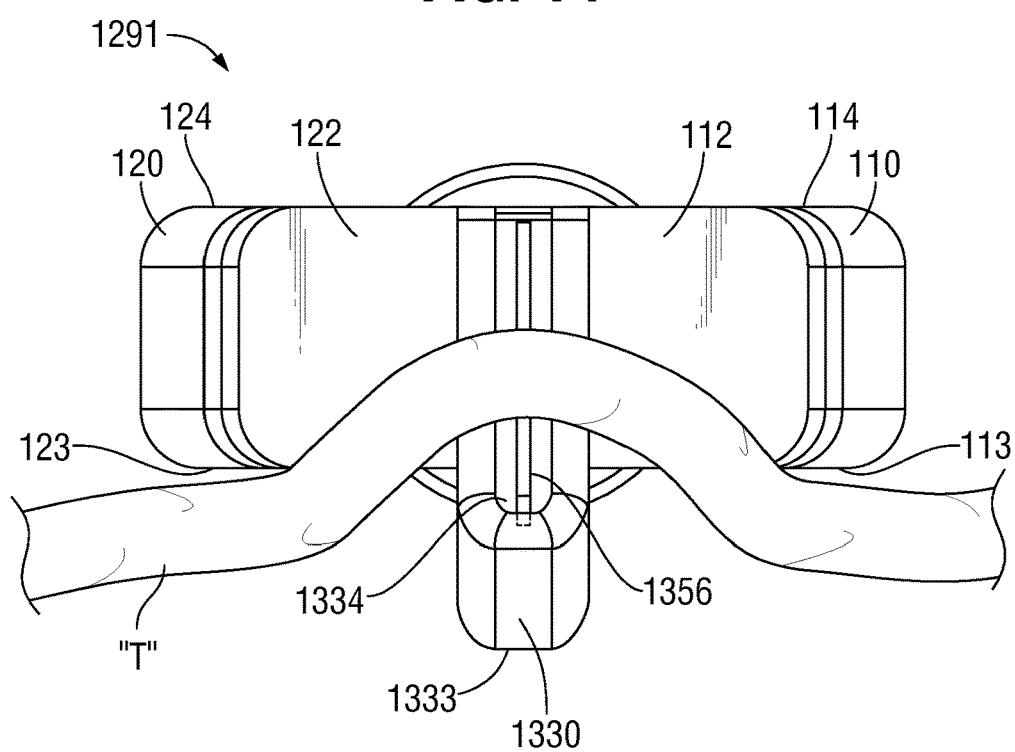
FIG. 15 is an enlarged, perspective view of the end-effector assembly of FIG. 14 shown with tissue disposed below the lower surfaces of the first and second jaw members and tissue overlying the cutting member disposed on the upper surface the third jaw member in accordance with an embodiment of the present disclosure.

In FIG. 14, the first and second jaw members 110 and 120 are disposed in spaced relation relative to the third jaw member 1330 as shown in FIG. 13, and the third jaw member 1330 is oriented at a downward angle. In this configuration, the bottom surface of the third jaw member 1330 is positioned below a plane defined by the bottom surfaces 113 and 123 of the first and second jaw members 110 and 120, respectively. In FIG. 15, tissue "T" is depicted overlying a portion of the cutting member 1356 disposed on the upper surface 1334 of the third jaw member 1330.

Figure 16:
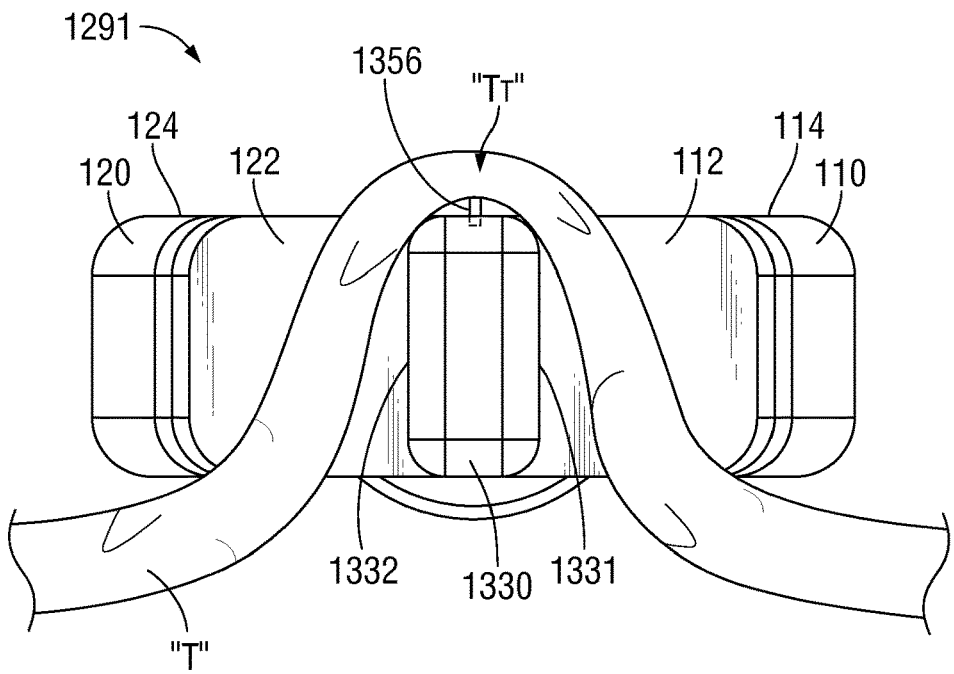
FIG. 16 is an enlarged, perspective view of the end-effector assembly of FIG. 15 disposed in the open configuration shown in FIG. 13, showing tissue disposed between the first and second jaw members and overlying the cutting member, in accordance with an embodiment of the present disclosure.

In FIG. 16, the first and second jaw members 110 and 120 are shown disposed in spaced relation relative to the third jaw member 1330, with tissue "T" disposed between the first and third sealing plates 112 and 1331 of the first and third jaw members 110 and 1330, respectively, and the second and fourth sealing plates 122 and 1332 of the second and third jaw members 120 and 1330, respectively, and tissue in tension "$T_T$" overlying a portion of the cutting member 1356 disposed on the upper surface 1334 of the third jaw member 1330.

Figure 17:
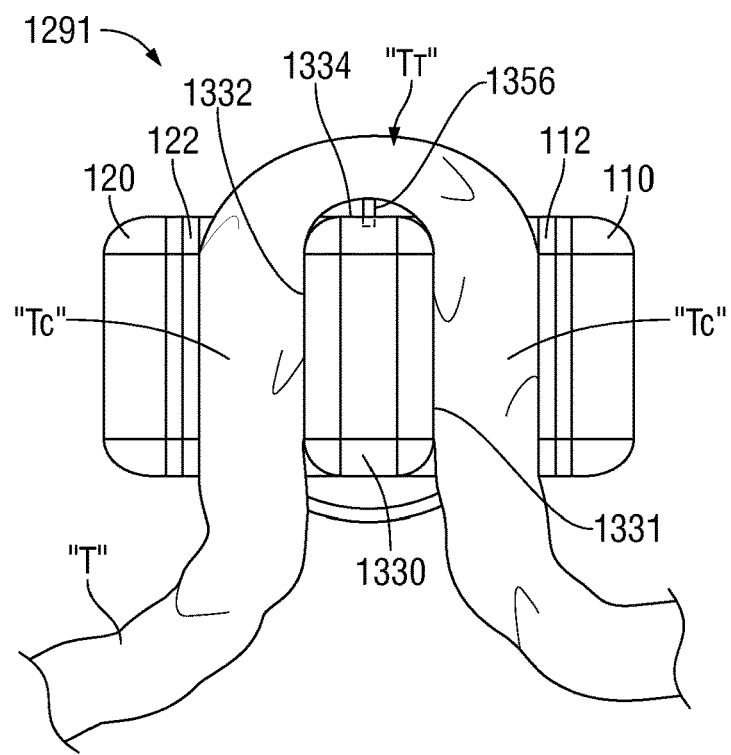
FIG. 17 is an enlarged, perspective view of the end-effector assembly of FIG. 16 showing the first and second jaw members in a closed configuration with sealed tissue in compression disposed between the electrically-conductive tissue-engaging surfaces of the third jaw member and the electrically-conductive tissue-engaging surfaces of the first and second jaw members, respectively, shown with tissue in tension overlying the cutting member, in accordance with an embodiment of the present disclosure.
Figure 18:
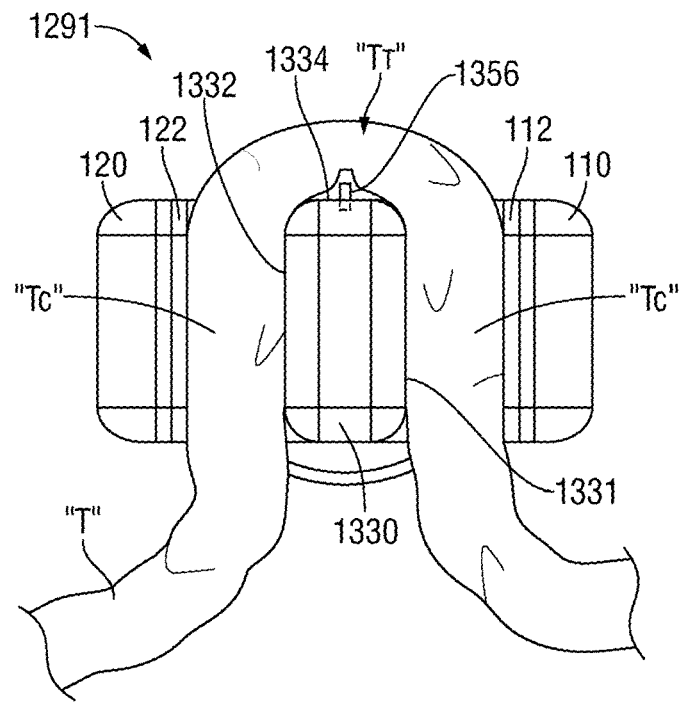
FIG. 18 is an enlarged, perspective view of the end-effector assembly of FIG. 17 shown with partially-severed tissue in tension disposed above the third jaw member in accordance with an embodiment of the present disclosure.

FIG. 17 shows the first and second jaw members 110 and 120 in a closed configuration with tissue in compression "$T_C$", e.g., vascular tissue, between the first and third sealing plates 112 and 1331 of the first and third jaw members 110 and 1330, respectively, and the second and fourth sealing plates 122 and 1332 of the second and third jaw members 120 and 1330, respectively, and with tissue in tension "$T_T$" overlying the cutting member 1356 disposed on the upper surface 1334 of the third jaw member 1330. When the first and second jaw members 110 and 120 are disposed in a closed configuration, e.g., to effect grasping of tissue "T", energy may be applied via the first, second, third and fourth sealing plates 112, 122, 1331 and 1332 to effect sealing of the tissue in compression "$T_C$". Once the tissue is sealed, the cutting member 1356 may be used to transect, dissect and/or coagulate the tissue in tension "$T_T$" overlying the upper surface 1334 of the third jaw member 1330. In FIG. 18, partially-cut tissue in tension "$T_T$" is illustratively depicted. In some embodiments, as shown in FIG. 18, the end-effector assembly 1291 is configured to allow the user to selectively apply tension in a particular direction, e.g., upward tension, to the tissue in tension "$T_T$" during treatment by the cutting member 1356. In some embodiments, the end-effector assembly 1291 is configured to provide a user capability to controllably move the first and second jaw members 110 and 120 laterally towards the third jaw member 1330 to progressively tension the tissue "$T_T$" overlying the upper surface 1334 of the third jaw member 1330.

Figure 19:
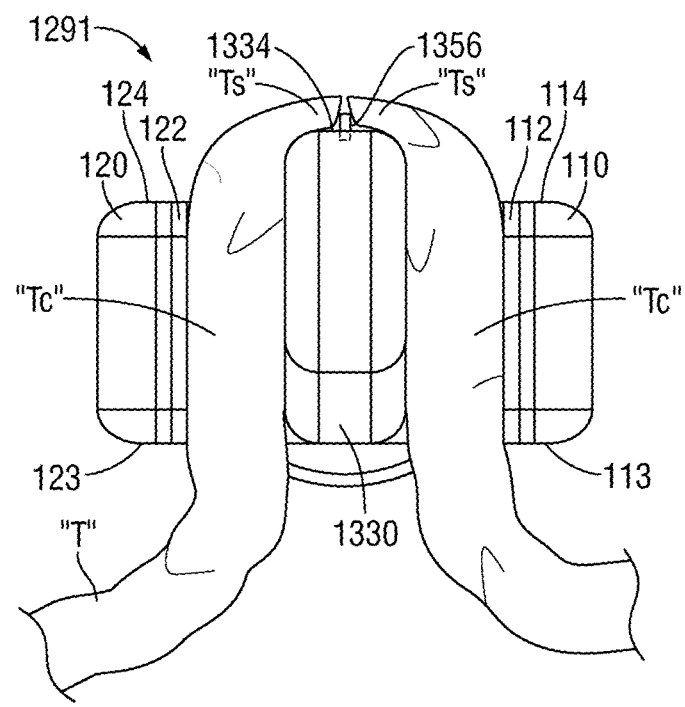
FIG. 19 is an enlarged, perspective view of the end-effector assembly of FIG. 18 showing the third jaw member disposed upwardly at a second angle, shown with tissue severed into two portions disposed above the upper surface the third jaw member, in accordance with an embodiment of the present disclosure.

In embodiments wherein the cutting member 1356 is an ultrasonic member, during a procedure, tension applied to the tissue in tension "$T_T$" may improve efficiency, e.g., increase the rate of dissection and/or coagulation, and/or otherwise improve the outcome. In an embodiment shown in FIG. 19, the end-effector assembly 1291 is configured to allow the user to effect movement of the third jaw member 1330, which changes the orientation of the cutting member 1356 disposed on the upper surface 1334 of the third jaw member 1330, e.g., to selectively apply tension to the tissue in tension "$T_T$" during treatment by the cutting member 1356. In FIG. 19, the end-effector assembly 1291 is shown with tissue in compression "$T_C$" between the first and second electrically-conductive tissue-engaging surfaces 112 and 122 and the first and second tissue-engaging surfaces of the third jaw member 1330, and severed tissue "$T_S$" disposed above the upper surface 1334 of the third jaw member 1330.

Hereinafter, methods of cutting tissue, in accordance with the present disclosure, are described with reference to FIGS. 20 and 21. It is to be understood that the steps of the methods provided herein may be performed in combination and in a different order than presented herein without departing from the scope of the disclosure.

Figure 20:
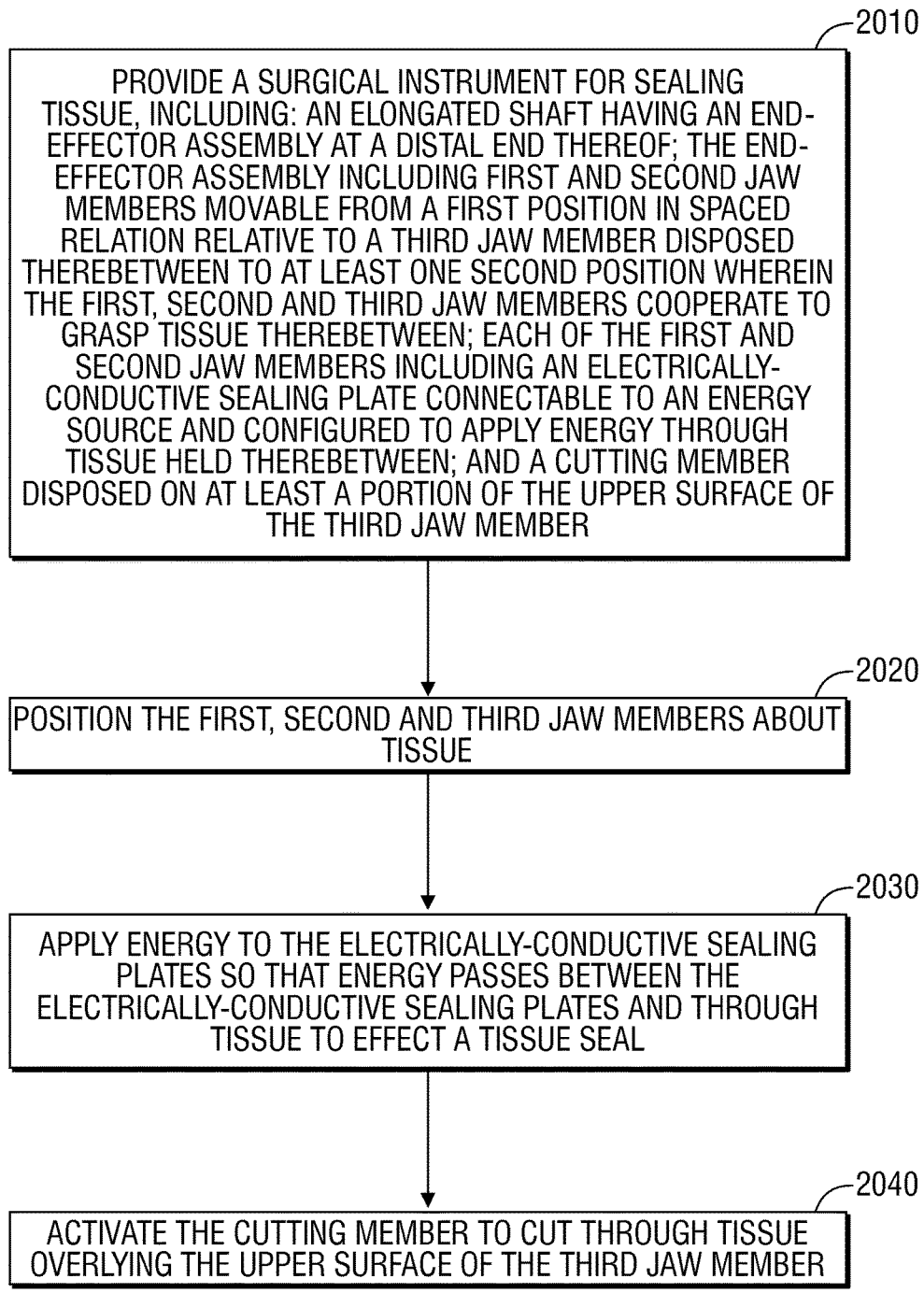
FIG. 20 is a flowchart illustrating a method of cutting tissue in accordance with an embodiment of the present disclosure.

FIG. 20 is a flowchart illustrating a method of cutting tissue according to an embodiment of the present disclosure. In step 2010, a surgical instrument 10 for sealing tissue is provided. The instrument 10 includes an elongated shaft 12 having an end-effector assembly 1291 at a distal end thereof. The end-effector 1291 assembly includes first and second jaw members 110 and 120 controllably movable from a first position in spaced relation relative to a third jaw member 1330 disposed therebetween to at least one second position closer to the third jaw member 1330 wherein the first, second and third jaw members 110, 120 and 1330, respectively, cooperate to grasp tissue therebetween, e.g., to control the amount of compression applied to tissue. Each of the first and second jaw members 110 and 120 includes an electrically-conductive sealing plate 112 and 122, respectively, connectable to an energy source 28 and configured to apply energy through tissue held therebetween. In some embodiments, the third jaw member 1330 includes electrically-conductive sealing plates 1331 and 1332. A cutting member 1356 is disposed on at least a portion of an upper surface of the third jaw member 1330.

In step 2020, the first, second and third jaw members 110, 120 and 1330, respectively, are positioned about tissue "T".

In step 2030, energy is applied to the electrically-conductive sealing plates 112, 122 so that energy passes between the electrically-conductive sealing plates 112, 122 and through tissue in compression "$T_C$" to effect a tissue seal. In some embodiments, wherein the third jaw member 1330 includes electrically-conductive sealing plates 1331 and 1332, during activation, energy passes between the electrically-conductive sealing plates 112 and 1331 and through tissue in compression "$T_C$" disposed therebetween, and/or energy passes between the electrically-conductive sealing plates 122 and 1332 and through tissue in compression "$T_C$" disposed therebetween.

In step 2040, the cutting member 1356 is activated to cut through tissue in tension "$T_T$" overlying the upper surface 1334 of the third jaw member 1330.

Figure 21:
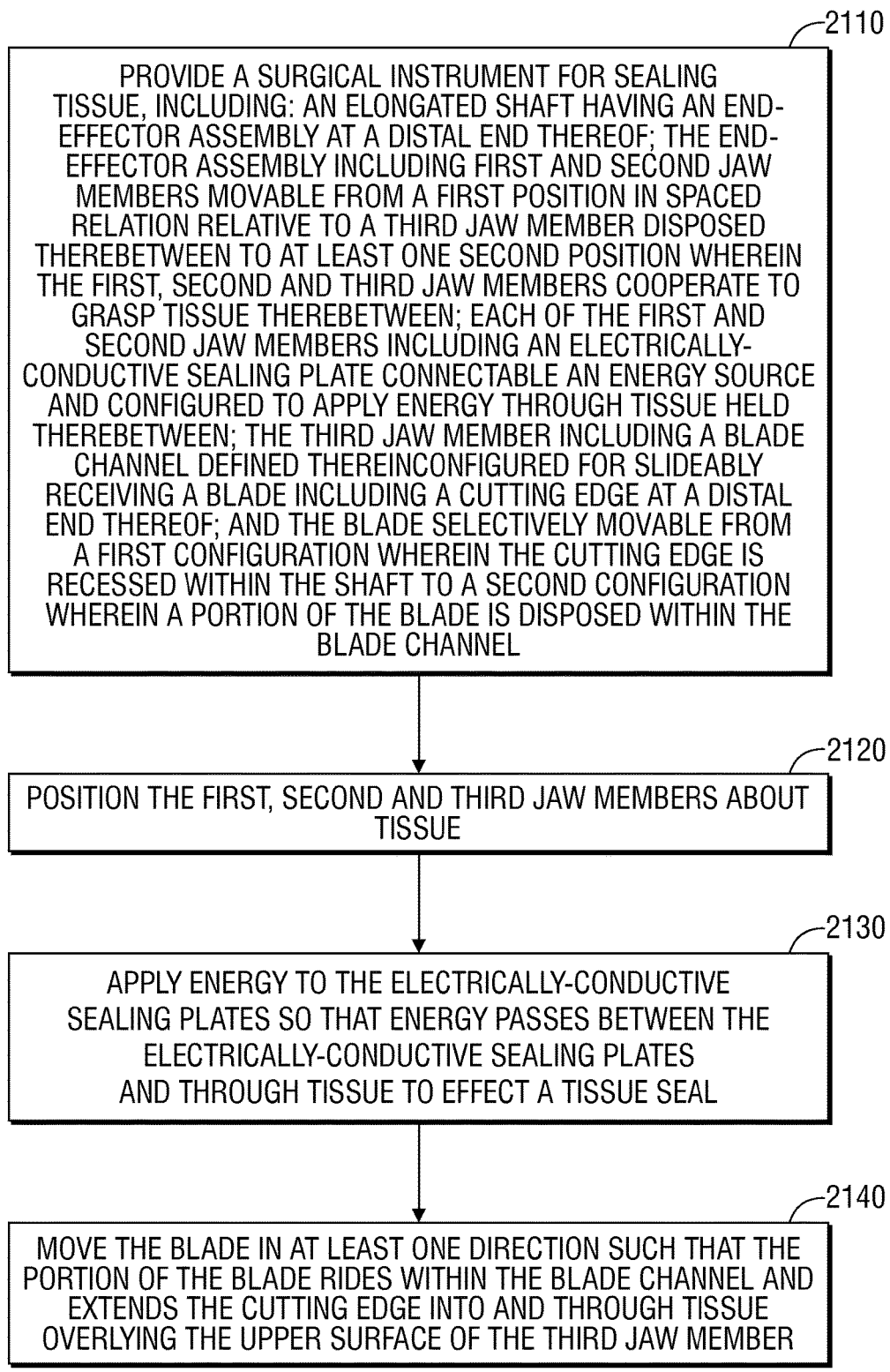
FIG. 21 is a flowchart illustrating a method of cutting tissue in accordance with another embodiment of the present disclosure.

FIG. 21 is a flowchart illustrating a method of cutting tissue according to an embodiment of the present disclosure. In step 2110, a surgical instrument 10 for sealing tissue is provided. The surgical instrument 10 includes an elongated shaft 712 having an end-effector assembly 791 at a distal end thereof. The end-effector 791 assembly includes first and second jaw members 110 and 120 controllably movable from a first position in spaced relation relative to a third jaw member 730 disposed therebetween to at least one second position closer to the third jaw member 730 wherein the first, second and third jaw members 110, 120 and 730, respectively, cooperate to grasp tissue therebetween, e.g., to control the amount of compression applied to tissue. Each of the first and second jaw members 110 and 120 includes an electrically-conductive sealing plate 112 and 122, respectively, connectable to an energy source 28 and configured to apply energy through tissue held therebetween. In some embodiments, the third jaw member 730 includes electrically-conductive sealing plates 731 and 732.

In some embodiments, the third jaw member 730 is configured to be controllably movable from a first configuration, wherein an upper surface 734 of the third jaw member 730 is disposed within a plane defined by the upper surfaces 114 and 124 of the first and second jaw members 110 and 120, respectively, to a second configuration, wherein the upper surface 734 of the third jaw member 730 is disposed below the plane defined by the upper surfaces 114 and 124 of the first and second jaw members 110 and 120. In some embodiments, the third jaw member 730 is configured to be controllably movable from a first configuration, wherein an upper surface 734 of the third jaw member 730 is disposed within a plane defined by the upper surfaces 114 and 124 of the first and second jaw members 110 and 120, respectively, to a third configuration, wherein the upper surface 734 of the third jaw member 730 is disposed above the plane defined by the upper surfaces 114 and 124 of the first and second jaw members 110 and 120.

In step 2120, the first, second and third jaw members 110, 120 and 730, respectively, are positioned about tissue "T".

In step 2130, energy is applied to the electrically-conductive sealing plates 112, 122 so that energy passes between the electrically-conductive sealing plates 112, 122 and through tissue in compression "$T_T$" to effect a tissue seal. In some embodiments, wherein the third jaw member 730 includes electrically-conductive sealing plates 731 and 732, during activation, energy passes between the electrically-conductive sealing plates 112 and 731 and through tissue in compression "$T_C$" disposed therebetween, and/or energy passes between the electrically-conductive sealing plates 122 and 732 and through tissue in compression "$T_C$" disposed therebetween.

In step 2140, the cutting member 756 is activated to cut through tissue in tension "$T_T$" overlying the upper surface of the third jaw member 730.

The above-described surgical instruments with an end-effector assembly including three jaw members are configured to allow the surgeon to move first and second jaw members from an open position, wherein the first and second jaw members are disposed in spaced relation relative to a third jaw member disposed therebetween, to a clamping or closed position, wherein the first, second and third jaw members, cooperate to grasp tissue therebetween. The above-described end-effector assemblies are configured to allow the first and second jaw members to be controllably movable relative to one another and/or relative to the third jaw member, e.g., to control the amount of compression applied to tissue. The above-described surgical instruments are configured to provide a user capability to controllably move the first and second jaw members laterally towards the third jaw member to progressively tension the tissue overlying the upper surface of the third jaw member.

The above-described surgical instruments are configured to allow the third jaw member to be controllably movable from a first configuration, wherein an upper surface of the third jaw member is substantially coplanar with the upper surfaces of the first and second jaw members, to a second configuration, wherein the upper surface of the third jaw member is disposed below (or above) a plane defined by the upper surfaces of the first and second jaw members.

The above-described surgical instruments may be suitable for sealing, cauterizing, coagulating/desiccating and/or cutting vessels and vascular tissue and may be suitable for utilization in endoscopic surgical procedures and/or suitable for utilization in open surgical applications. The above-described surgical instruments with an end-effector assembly including three jaw members may be configured for use with a variety of energy sources.

Although embodiments have been described in detail with reference to the accompanying drawings for the purpose of illustration and description, it is to be understood that the inventive processes and apparatus are not to be construed as limited thereby. It will be apparent to those of ordinary skill in the art that various modifications to the foregoing embodiments may be made without departing from the scope of the disclosure.

What is claimed is:

1. A method of cutting tissue, comprising:
providing a surgical instrument for sealing tissue, including:
an end-effector assembly including first and second jaw members controllably movable from a first position wherein the first and second jaw members are disposed in spaced relation relative to a third jaw member disposed therebetween to at least one second position closer to the third jaw member wherein the first, second and third jaw members cooperate to grasp tissue therebetween, the end-effector assembly configured to controllably move the first and second jaw members laterally towards the third jaw member to progressively tension tissue overlying the upper surface of the third jaw member; and
a cutting member associated with an upper surface of the third jaw member;
positioning the first, second and third jaw members about tissue such that the upper surface of the third jaw member is coplanar with upper surfaces of the first and second jaw members and the upper surface of the third jaw member is disposed above a plane defined by bottom surfaces of the first and second jaw members;
applying energy to electrically-conductive sealing plates so that energy passes between the electrically-conductive sealing plates and through tissue to effect a tissue seal; and
activating the cutting member to cut through tissue overlying the upper surface of the third jaw member.

2. The method of cutting tissue of claim 1, wherein the providing includes the cutting member configured to outwardly extend from the upper surface of the third jaw member.

3. The method of cutting tissue of claim 1, wherein the providing includes the cutting member is an ultrasonic member configured to treat tissue.

4. The method of cutting tissue of claim 1, wherein the providing includes the third jaw member configured to be controllably movable from a first configuration, wherein the upper surface of the third jaw member is coplanar with the upper surfaces of the first and second jaw members, to a second configuration, wherein the upper surface of the third jaw member is disposed below a plane defined by the upper surfaces of the first and second jaw members.

5. The method of cutting tissue of claim 1, wherein the providing includes the third jaw member configured to be controllably movable from a first configuration, wherein the upper surface of the third jaw member is coplanar with the upper surfaces of the first and second jaw members, to a third configuration, wherein the upper surface of the third jaw member is disposed above a plane defined by the upper surfaces of the first and second jaw members.

6. A method of cutting tissue, comprising:
providing a surgical instrument for sealing tissue, including:
an elongated shaft having an end-effector assembly at a distal end thereof;
the end-effector assembly including first and second jaw members controllably movable from a first position in spaced relation relative to a third jaw member disposed therebetween to at least one second position closer to the third jaw member wherein the first, second and third jaw members cooperate to grasp tissue therebetween, the end-effector assembly configured to controllably move the first and second jaw members laterally towards the third jaw member to progressively tension tissue overlying the upper surface of the third jaw member;
each of the first and second jaw members including an electrically-conductive sealing plate connectable to an energy source and configured to apply energy through tissue held therebetween;
the third jaw member including a blade channel defined therein configured to slideably receive a blade including a cutting edge at a distal end thereof, the blade selectively movable from a first configuration wherein the cutting edge is recessed within the elongated shaft to a second configuration wherein a portion of the blade is disposed within the blade channel;
positioning the first, second and third jaw members about tissue such that an upper surface of the third jaw member is coplanar with upper surfaces of the first and second jaw members and the upper surface of the third jaw member is disposed above a plane defined by bottom surfaces of the first and second jaw members;
applying energy to the electrically-conductive sealing plates so that energy passes between the electrically-conductive sealing plates and through tissue to effect a tissue seal; and
moving the blade in at least one direction such that the portion of the blade rides within the blade channel and extends the cutting edge into and through tissue overlying the upper surface of the third jaw member.

7. The method of cutting tissue of claim 6, wherein the providing includes the blade includes a blade bar and the cutting edge is disposed at a distal end of the knife bar.

8. The method of cutting tissue of claim 7, wherein the providing includes the blade channel configured to slideably receive a portion of the blade bar including a bottom edge thereof.

9. The method of cutting tissue of claim 6, wherein the providing includes the third jaw member configured to be controllably movable from a first configuration, wherein the upper surface of the third jaw member is coplanar with the upper surfaces of the first and second jaw members, to a second configuration, wherein the upper surface of the third jaw member is disposed below a plane defined by the upper surfaces of the first and second jaw members.

10. The method of cutting tissue of claim 6, wherein the providing includes the third jaw member configured to be controllably movable from a first configuration, wherein the upper surface of the third jaw member is coplanar with the upper surfaces of the first and second jaw members, to a third configuration, wherein the upper surface of the third jaw member is disposed above a plane defined by the upper surfaces of the first and second jaw members.

11. The method of cutting tissue of claim 6, wherein the providing includes the electrosurgical instrument further includes a knife cover protruding outwardly of an outer circumferential surface of the elongated shaft.

12. The method of cutting tissue of claim 1, further comprising tensioning tissue by moving the first jaw member in a first direction toward the third jaw member and moving the second jaw member in a second direction opposite the first direction toward the third jaw member.

13. The method of cutting tissue of claim 6, further comprising tensioning tissue by moving the first jaw member in a first direction toward the third jaw member and moving the second jaw member in a second direction opposite the first direction toward the third jaw member.

14. A method of cutting tissue, comprising:
providing a surgical instrument for sealing tissue, including:
an end-effector assembly including first and second jaw members movable from a first position wherein the first and second jaw members are disposed in spaced relation relative to a third jaw member disposed therebetween to at least one second position closer to the third jaw member wherein the first, second and third jaw members cooperate to grasp tissue therebetween, wherein the first, second, and third jaw members are movable to a position where an upper surface of the third jaw member is coplanar with upper surfaces of the first and second jaw members and the upper surface of the third jaw member is disposed above a plane defined by bottom surfaces of the first and second jaw members;
positioning the first, second and third jaw members about tissue to grasp tissue therebetween;
tensioning the grasped tissue by moving the first jaw member in a first direction toward the third jaw member and moving the second jaw member in a second direction opposite the first direction toward the third jaw member.

15. The method of cutting tissue of claim 14, further comprising applying energy to electrically-conductive sealing plates of the first and second jaw members so that energy passes between the electrically-conductive sealing plates and through tissue to effect a tissue seal.

16. The method of cutting tissue of claim 14, wherein the surgical instrument further includes a cutting member associated with the upper surface of the third jaw member.

17. The method of cutting tissue of claim 16, further comprising activating the cutting member to cut tissue overlying the upper surface of the third jaw member.

18. A method of cutting tissue, comprising:
providing a surgical instrument for sealing tissue, including:
an end-effector assembly including first and second jaw members controllably movable from a first position wherein the first and second jaw members are disposed in spaced relation relative to a third jaw member disposed therebetween to at least one second position closer to the third jaw member wherein the first, second and third jaw members cooperate to grasp tissue therebetween; and
a cutting member associated with an upper surface of the third jaw member;
positioning the first, second and third jaw members about tissue such that the upper surface of the third jaw member is coplanar with upper surfaces of the first and second jaw members and the upper surface of the third jaw member is disposed above a plane defined by bottom surfaces of the first and second jaw members;

tensioning tissue by moving the first jaw member in a first direction toward the third jaw member and moving the second jaw member in a second direction opposite the first direction toward the third jaw member;

applying energy to electrically-conductive sealing plates so that energy passes between the electrically-conductive sealing plates and through tissue to effect a tissue seal; and activating the cutting member to cut through tissue overlying the upper surface of the third jaw member.

19. A method of cutting tissue, comprising:

providing a surgical instrument for sealing tissue, including:

an elongated shaft having an end-effector assembly at a distal end thereof;

the end-effector assembly including first and second jaw members controllably movable from a first position in spaced relation relative to a third jaw member disposed therebetween to at least one second position closer to the third jaw member wherein the first, second and third jaw members cooperate to grasp tissue therebetween;

each of the first and second jaw members including an electrically-conductive sealing plate connectable to an energy source and configured to apply energy through tissue held therebetween;

the third jaw member including a blade channel defined therein configured to slideably receive a blade including a cutting edge at a distal end thereof, the blade selectively movable from a first configuration wherein the cutting edge is recessed within the elongated shaft to a second configuration wherein a portion of the blade is disposed within the blade channel;

positioning the first, second and third jaw members about tissue such that an upper surface of the third jaw member is coplanar with upper surfaces of the first and second jaw members and the upper surface of the third jaw member is disposed above a plane defined by bottom surfaces of the first and second jaw members;

tensioning tissue by moving the first jaw member in a first direction toward the third jaw member and moving the second jaw member in a second direction opposite the first direction toward the third jaw member;

applying energy to the electrically-conductive sealing plates so that energy passes between the electrically-conductive sealing plates and through tissue to effect a tissue seal; and moving the blade in at least one direction such that the portion of the blade rides within the blade channel and extends the cutting edge into and through tissue overlying the upper surface of the third jaw member.

* * * * *